US008389227B2

(12) United States Patent
Lopez et al.

(10) Patent No.: US 8,389,227 B2
(45) Date of Patent: Mar. 5, 2013

(54) METHOD FOR DIAGNOSING CANCERS EXPRESSING THE HER2 RECEPTOR OR ITS TRUNCATED VARIANTS

(75) Inventors: Joaquin Arribas Lopez, Cerdanyola del Valles (ES); Kim Pedersen, Barcelona (ES); Pier-Davide Angellini, Barcelona (ES); Josep Liuis Parra Palau, Barcelona (ES); Sirle Laos, Torredembarra (ES); Jose Baselga Torres, Barcelona (ES)

(73) Assignees: Fundacio Privada Institut de Recerca Hospital Universitari Vall Hebron, Barcelona (ES); Fundacio Privada Institucio Catalana de Recera I Estudis Avancats, Barcelona (ES); Fundacio Privada Institut d'Investigacio Oncologica de Vall Hebron, Barcelona (ES)

( * ) Notice: Subject to any disclaimer, the term of this patent is extended or adjusted under 35 U.S.C. 154(b) by 584 days.

(21) Appl. No.: 12/479,035

(22) Filed: Jun. 5, 2009

(65) Prior Publication Data
US 2009/0311262 A1 Dec. 17, 2009

(51) Int. Cl.
*C12P 21/08* (2006.01)
*C07K 16/30* (2006.01)
*C07K 16/28* (2006.01)
*G01N 33/574* (2006.01)
*G01N 33/573* (2006.01)
*G01N 33/567* (2006.01)
*G01N 33/50* (2006.01)
*C07K 17/16* (2006.01)

(52) U.S. Cl. ........ 435/7.23; 435/7.1; 435/7.21; 435/7.4; 436/501; 436/503; 436/63; 436/64; 530/387.1; 530/387.7; 530/387.9; 530/388.1; 530/388.22; 530/388.8; 530/388.85; 530/389.1; 530/389.7; 530/402; 530/403; 530/806; 530/808

(58) Field of Classification Search ............... 530/387.1, 530/387.7, 387.9, 388.1, 388.22, 388.8, 388.85, 530/389.1, 389.7, 402, 403, 806, 808; 435/7.1, 435/7.21, 7.23, 7.4; 436/501, 503, 63, 64
See application file for complete search history.

(56) References Cited

U.S. PATENT DOCUMENTS

| 7,371,376 | B1 | 5/2008 | Fendly | |
| 7,829,297 | B2* | 11/2010 | Spector et al. | 435/7.1 |
| 2010/0143927 | A1* | 6/2010 | Sperinde et al. | 435/6 |

FOREIGN PATENT DOCUMENTS

| WO | 89/06692 | 7/1989 |
| WO | 96/06863 | 2/1998 |
| WO | 99/31140 | 6/1999 |
| WO | 00/69460 | 11/2000 |
| WO | 01/15730 | 3/2001 |

OTHER PUBLICATIONS

Anido et al., EMBO J., 25:3234-3244 (2006).
Arribas et al., Chem. Rev., 102:4627-4637 (2002).
Black, FASEB J., 6:680-685 (1992).
Brantley-Sieders et al., J. Clin. Invest., 118:64-78 (2008).
Burgess et al., Mol. Cell, 12:541-552 (2003).
Christianson et al., Cancer Res., 58:5123-5129 (1998).
Citri et al., Nat. Rev., 7:505-516 (2006).
Codony-Servat et al., Cancer Res., 59:1196-1201 (1999).
Ding et al., World J. Gastroenterol., 10:2735-2739 (2004).
Garrett et al., Mol. Cell, 11:495-505 (2003).
Gentile et al., Int. J. Dev. Biol., 48:451-456 (2004).
Giri et al., Mol. Cell. Biol., 25:11005-11018 (2005).
Gupta et al., Nature, 446:765-770 (2007).
Guy et al., Proc. Natl. Acad. Sci. USA, 89:10578-10582 (1992).
Hsu et al., J. Biol. Chem., 282:10432-10440 (2007).
Hynes et al., Nat. Rev., 5:341-354 (2005).
Kang et al., Cancer Cell, 3:537-549 (2003).
Kochetov, BioEssays, 30:683-691 (2008).
Kwong et al., Mol. Carcinogen., 23:62-68 (1998).
Lee et al., J. Biol. Chem., 277:6313-6323 (2002).
Lin et al., Oncogene, 6:639-643 (1990).
Linggi et al., J. Biol. Chem., 281:25373-25380 (2006).
Liu et al., Cancer Biol. Ther., 5:e1-e8 (2006).
Miller et al., Proc. Natl. Acad. Sci. USA, 102:13550-13555 (2005).
Molina et al., Cancer Res., 61:4744-4749 (2001).
Molina et al., Clin. Cancer Res., 8:347-353 (2002).
Muller et al., Cell, 54:105-115 (1988).
Ni et al., Science, 294:2179-2181 (2001).
Padua et al., Cell, 133:66-77 (2008).
Pawitan et al., Breast Cancer Res., 7:R953-R964 (2005).
Pupa et al., Oncogene, 8:2917-2923 (1993).
Saez et al., Clin. Cancer Res., 12:424-431 (2006).
Scaltriti et al., J. Natl. Cancer Inst., 99:628-638 (2007).
Shigematsu et al., Cancer Res., 65:1642-1646 (2005).
Siegel et al., Mol. Cell Biol., 14:7068-7077 (1994).
Siegel et al., Proc. Natl. Acad. Sci. USA, 93:8878-8883 (1996).
Siegel et al., EMBO J., 18:2149-2164 (1999).
Ursini-Siegel et al., Nat. Rev., 7:389-397 (2007).

(Continued)

*Primary Examiner* — Alana Harris Dent
*Assistant Examiner* — Anne Holleran
(74) *Attorney, Agent, or Firm* — McAndrews, Held & Malloy Ltd.

(57) ABSTRACT

The present invention relates to a method of diagnosis and therapy of cancers expressing the HER2 receptor.

The invention provides antibodies or fragments thereof that recognizes an epitope of a HER2 receptor truncated form, said epitope being defined by a sequence included in SEQ ID NO: 2.

The invention also provides a method of cancer diagnosis, which comprises the detection of the presence of the HER2 receptor truncated form consisting of the amino acid sequence SEQ ID NO: 1 in a patient sample.

18 Claims, 9 Drawing Sheets

OTHER PUBLICATIONS

Vidal et al., J. Biol. Chem., 280:19777-19783 (2005).
Wang et al., Cancer Cell, 6:251-261 (2004).
Williams et al., J. Cell Biol., 167:469-478 (2004).
Xia et al., Oncogene, 23:646-653 (2004).
Yarden et al., Nat. Rev. Mol. Cell Biol., 2:127-137 (2001).
Yuan et al., Protein Expr. Purif., 29:217-222 (2003).
Zabrecky et al., J. Biol. Chem., 266:1716-1720 (1991).

* cited by examiner

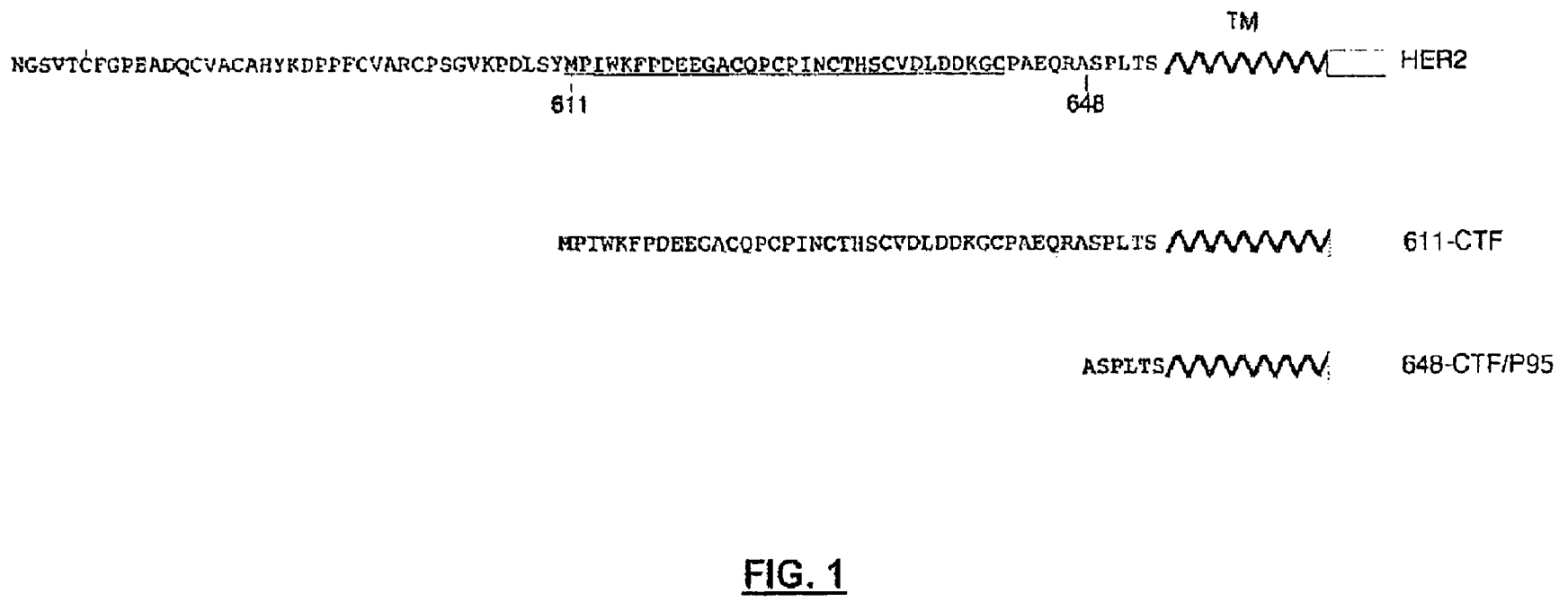

NGSVTCFGPEADQCVACAHYKDFFFCVARCPSGVKPDLSYMPIWKFFPDEEGACQPCPINCTHSCVDLDDKGCPAEQRASPLTS 〰〰〰〰〰 HER2
                                              611                      648                    TM

MPIWKFPDEEGACQPCPINCTISCVDLDDKGCPAEQRASPLTS 〰〰〰〰〰 611-CTF

ASPLTS 〰〰〰〰〰 648-CTF/P95

FIG. 1

```
                        SEQUENCE LISTING

<160> NUMBER OF SEQ ID NOS: 8

<210> SEQ ID NO 1
<211> LENGTH: 645
<212> TYPE: PRT
<213> ORGANISM: Homo sapiens
<220> FEATURE:
<221> NAME/KEY: MISC_FEATURE
<223> OTHER INFORMATION: Truncated form or Carboxy Terminal Fragment
      (CTF) of the human protein HER2

<400> SEQUENCE: 1

Met Pro Ile Trp Lys Phe Pro Asp Glu Glu Gly Ala Cys Gln Pro Cys
1               5                   10                  15

Pro Ile Asn Cys Thr His Ser Cys Val Asp Leu Asp Asp Lys Gly Cys
                20                  25                  30
```

-continued

```
Pro Ala Glu Gln Arg Ala Ser Pro Leu Thr Ser Ile Ile Ser Ala Val
            35                  40                  45

Val Gly Ile Leu Leu Val Val Leu Gly Val Val Phe Gly Ile Leu
 50                  55                  60

Ile Lys Arg Arg Gln Gln Lys Ile Arg Lys Tyr Thr Met Arg Arg Leu
 65                  70                  75                  80

Leu Gln Glu Thr Glu Leu Val Glu Pro Leu Thr Pro Ser Gly Ala Met
                 85                  90                  95

Pro Asn Gln Ala Gln Met Arg Ile Leu Lys Glu Thr Glu Leu Arg Lys
            100                 105                 110

Val Lys Val Leu Gly Ser Gly Ala Phe Gly Thr Val Tyr Lys Gly Ile
            115                 120                 125

Trp Ile Pro Asp Gly Glu Asn Val Lys Ile Pro Val Ala Ile Lys Val
            130                 135                 140

Leu Arg Glu Asn Thr Ser Pro Lys Ala Asn Lys Glu Ile Leu Asp Glu
145                 150                 155                 160

Ala Tyr Val Met Ala Gly Val Gly Ser Pro Tyr Val Ser Arg Leu Leu
                165                 170                 175

Gly Ile Cys Leu Thr Ser Thr Val Gln Leu Val Thr Gln Leu Met Pro
            180                 185                 190

Tyr Gly Cys Leu Leu Asp His Val Arg Glu Asn Arg Gly Arg Leu Gly
            195                 200                 205

Ser Gln Asp Leu Leu Asn Trp Cys Met Gln Ile Ala Lys Gly Met Ser
            210                 215                 220

Tyr Leu Glu Asp Val Arg Leu Val His Arg Asp Leu Ala Ala Arg Asn
225                 230                 235                 240

Val Leu Val Lys Ser Pro Asn His Val Lys Ile Thr Asp Phe Gly Leu
                245                 250                 255

Ala Arg Leu Leu Asp Ile Asp Glu Thr Glu Tyr His Ala Asp Gly Gly
            260                 265                 270

Lys Val Pro Ile Lys Trp Met Ala Leu Glu Ser Ile Leu Arg Arg Arg
            275                 280                 285

Phe Thr His Gln Ser Asp Val Trp Ser Tyr Gly Val Thr Val Trp Glu
            290                 295                 300

Leu Met Thr Phe Gly Ala Lys Pro Tyr Asp Gly Ile Pro Ala Arg Glu
305                 310                 315                 320

Ile Pro Asp Leu Leu Glu Lys Gly Glu Arg Leu Pro Gln Pro Pro Ile
                325                 330                 335

Cys Thr Ile Asp Val Tyr Met Ile Met Val Lys Cys Trp Met Ile Asp
            340                 345                 350

Ser Glu Cys Arg Pro Arg Phe Arg Glu Leu Val Ser Glu Phe Ser Arg
            355                 360                 365

Met Ala Arg Asp Pro Gln Arg Phe Val Val Ile Gln Asn Glu Asp Leu
            370                 375                 380

Gly Pro Ala Ser Pro Leu Asp Ser Thr Phe Tyr Arg Ser Leu Leu Glu
385                 390                 395                 400

Asp Asp Asp Met Gly Asp Leu Val Asp Ala Glu Glu Tyr Leu Val Pro
                405                 410                 415

Gln Gln Gly Phe Phe Cys Pro Asp Pro Ala Pro Gly Ala Gly Gly Met
            420                 425                 430

Val His His Arg His Arg Ser Ser Ser Thr Arg Ser Gly Gly Gly Asp
            435                 440                 445
```

```
Leu Thr Leu Gly Leu Glu Pro Ser Glu Glu Ala Pro Arg Ser Pro
    450                 455                 460
Leu Ala Pro Ser Glu Gly Ala Gly Ser Asp Val Phe Asp Gly Asp Leu
465                 470                 475                 480
Gly Met Gly Ala Ala Lys Gly Leu Gln Ser Leu Pro Thr His Asp Pro
                485                 490                 495
Ser Pro Leu Gln Arg Tyr Ser Glu Asp Pro Thr Val Pro Leu Pro Ser
            500                 505                 510
Glu Thr Asp Gly Tyr Val Ala Pro Leu Thr Cys Ser Pro Gln Pro Glu
        515                 520                 525
Tyr Val Asn Gln Pro Asp Val Arg Pro Gln Pro Ser Pro Arg Glu
    530                 535                 540
Gly Pro Leu Pro Ala Ala Arg Pro Ala Gly Ala Thr Leu Glu Arg Pro
545                 550                 555                 560
Lys Thr Leu Ser Pro Gly Lys Asn Gly Val Val Lys Asp Val Phe Ala
                565                 570                 575
Phe Gly Gly Ala Val Glu Asn Pro Glu Tyr Leu Thr Pro Gln Gly Gly
            580                 585                 590
Ala Ala Pro Gln Pro His Pro Pro Ala Phe Ser Pro Ala Phe Asp
    595                 600                 605
Asn Leu Tyr Tyr Trp Asp Gln Asp Pro Pro Glu Arg Gly Ala Pro Pro
610                 615                 620
Ser Thr Phe Lys Gly Thr Pro Thr Ala Glu Asn Pro Glu Tyr Leu Gly
625                 630                 635                 640
Leu Asp Val Pro Val
                645

<210> SEQ ID NO 2
<211> LENGTH: 42
<212> TYPE: PRT
<213> ORGANISM: Homo sapiens
<220> FEATURE:
<221> NAME/KEY: MISC_FEATURE
<223> OTHER INFORMATION: Epitope of a truncated form of the human HER2
      protein

<400> SEQUENCE: 2

Met Pro Ile Trp Lys Phe Pro Asp Glu Glu Gly Ala Cys Gln Pro Cys
1               5                   10                  15
Pro Ile Asn Cys Thr His Ser Cys Val Asp Leu Asp Asp Lys Gly Cys
            20                  25                  30
Pro Ala Glu Gln Arg Ala Ser Pro Leu Thr
        35                  40

<210> SEQ ID NO 3
<211> LENGTH: 32
<212> TYPE: PRT
<213> ORGANISM: Homo sapiens
<220> FEATURE:
<221> NAME/KEY: MISC_FEATURE
<223> OTHER INFORMATION: Epitope of a truncated form of the human HER2
      protein

<400> SEQUENCE: 3

Met Pro Ile Trp Lys Phe Pro Asp Glu Glu Gly Ala Cys Gln Pro Cys
1               5                   10                  15
Pro Ile Asn Cys Thr His Ser Cys Val Asp Leu Asp Asp Lys Gly Cys
            20                  25                  30
```

```
<210> SEQ ID NO 4
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Synthetic peptide derived from an epitope of a
      truncated form of the human HER2 protein

<400> SEQUENCE: 4

Met Pro Ile Trp Lys Phe Pro Asp Glu Glu Gly Ala Ser Gln Pro Ser
1               5                   10                  15

Pro Ile Asn Ser Thr His Ser Ser Val Asp Leu Asp Lys Gly Cys
            20                  25                  30

<210> SEQ ID NO 5
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Synthetic peptide derived from an epitope of a
      truncated form of the human HER2 protein

<400> SEQUENCE: 5

Met Pro Ile Trp Lys Phe Pro Asp Glu Glu Gly Ala Ser
1               5                   10

<210> SEQ ID NO 6
<211> LENGTH: 83
<212> TYPE: PRT
<213> ORGANISM: Homo sapiens
<220> FEATURE:
<221> NAME/KEY: MISC_FEATURE
<223> OTHER INFORMATION: Amino acids 571 through 653 of HER2 receptor
      protein

<400> SEQUENCE: 6

Asn Gly Ser Val Thr Cys Phe Gly Pro Glu Ala Asp Gln Cys Val Ala
1               5                   10                  15

Cys Ala His Tyr Lys Asp Pro Pro Phe Cys Val Ala Arg Cys Pro Ser
            20                  25                  30

Gly Val Lys Pro Asp Leu Ser Tyr Met Pro Ile Trp Lys Phe Pro Asp
        35                  40                  45

Glu Glu Gly Ala Cys Gln Pro Cys Pro Ile Asn Cys Thr His Ser Cys
    50                  55                  60

Val Asp Leu Asp Asp Lys Gly Cys Pro Ala Glu Gln Arg Ala Ser Pro
65                  70                  75                  80

Leu Thr Ser

<210> SEQ ID NO 7
<211> LENGTH: 6
<212> TYPE: PRT
<213> ORGANISM: Homo sapiens
<220> FEATURE:
<221> NAME/KEY: MISC_FEATURE
<223> OTHER INFORMATION: Amino acids 648-653 of HER2 protein

<400> SEQUENCE: 7

Ala Ser Pro Leu Thr Ser
1               5
```

```
<210> SEQ ID NO 8
<211> LENGTH: 11
<212> TYPE: PRT
<213> ORGANISM: Homo sapiens
<220> FEATURE:
<221> NAME/KEY: MISC_FEATURE
<223> OTHER INFORMATION: 611-CTF common epitope for antibodies 32H2 and
      20F4.

<400> SEQUENCE: 8

Met Pro Ile Trp Lys Phe Pro Asp Glu Glu Gly
1               5                   10
```

METHOD FOR DIAGNOSING CANCERS EXPRESSING THE HER2 RECEPTOR OR ITS TRUNCATED VARIANTS

The present application claims benefit of priority of Spanish Application No. P200801652, which was filed Jun. 8, 2008. The entire text of the aforementioned application is incorporated herein by reference in its entirety.

The present invention relates to a method of diagnosis in isolated samples of cancers expressing the HER2 receptor. The invention also provides compounds for use in the early diagnosis and identification of the cancer as well as for use in therapy.

BACKGROUND ART

HER2 (also known as c-erbB2, ErbB2 or Neu) is a type I transmembrane protein belonging to the family of epidermal growth factor receptors or EGFR, also known as HER1 or ErbB1. Two additional members, HER3 and HER4 complete this family. When HER1, 3 or 4 binds to an EGF-type ligand, its extracellular domain adopts the conformation referred to as "open", which allows the formation of homodimers and heterodimers. Even if it does not bind to any ligand, HER2 also interacts with other HER receptors linked to a ligand, due to the fact that its extracellular domain is constitutively in "open" conformation.

The dimerisation directed by the extracellular domain leads to interaction of the intracellular kinase of HER receptors and to the subsequent transphosphorylation of some tyrosine residues. These phosphotyrosines, act as couplers of a group of intracellular phosphotyrosine-binding proteins. The interactions established at the plasmatic membrane are transduced to the cell nucleus by means of different signalling routes, such as the protein kinase route activated by mitogen activated protein kinase (MAPK), the protein kinase route activated by stress (JNK), phospholipase C gamma, etc. All of these signalling circuits control the expression of genes that act in a coordinated way to modify determining aspects of the state, of the cell, such as cell proliferation, migration, survival and adhesion. Thus, depending on the cell context, activation of the HER receptors results in a dramatic cell response, which can range from transformation into a malignant cell to a premature senescence.

In addition to the canonical signalling mode, the HER receptors or fragments thereof can be endocyted and transported to the nucleus, where they can directly regulate the expression of certain genes. This fact has been observed for the specific case of HER2 (Wang et al., "Binding at and transactivation of the COX-2 promoter by nuclear tyrosine kinase receptor ErbB-2", *Cancer Cell*—2004, Vol. 6, pp. 251-261), as well as for a carboxy terminal fragment (CTF), which consists of a HER4 receptor truncated form, which includes the entire cytoplasmic part (Linggi et al., "ErbB-4 s80 intracellular domain abrogates ETO2-dependent transcriptional repression", *J. Biological Chemistry*—2006, Vol. 281, pp. 25373-25380).

In human breast tumours, a series of carboxy terminal fragments or CTFs has been often found, which are assumed to include the transmembrane and cytoplasmic domains of HER2. (Molina et al, "NH(2)-terminal truncated HER2 protein but not full-length receptor is associated with nodal metastasis in human breast cancer", *Clinical Cancer Research*—2002, Vol. 8, pp. 347-353). It is also known that patients with breast cancer expressing the HER2 CTFs, or what comes to be the same truncated forms which do not include the N-terminal end of HER2 (HER2 CTFs), have a greater probability of developing metastasis (Molina et al. 2002—supra) and a worse prognosis than those patients who mainly express the complete form of HER2 (Saez et al., "p95HER2 predicts worse outcome in patients with HER2-positive breast cancer", *Clinical Cancer Research*—2006, Vol. 12, pp. 424-431).

Therefore, it is very important to be able to detect the presence of HER2 in tumours on time and even more to determine whether it is in a complete or truncated (CTF) form.

Nowadays, at the level of routine clinical tests antibodies are used to detect the presence of the complete form of HER2, in order to determine the type of breast tumour in question. In the event of detecting the presence of HER2, the recommended therapy consists of administering therapeutic monoclonal antibodies, such as Genentech's trastuzumab. The use of this monoclonal antibody for the treatment of cancer is described in the application WO 8906692 on behalf of Genentech. WO 8906692 describes monoclonal or polyclonal antibodies directed against the extracellular region of HER2, this extracellular region matching with the complete external part of the protein, which is its N-terminal end. As previously mentioned, the epitopes recognised by the antibodies cited in WO 8906692 are antigenic regions of the extracellular domain of the HER2 complete form and are not included in truncated forms or carboxy terminal fragments of HER2. Therefore, with the antibodies and the diagnosis method described in WO 8906692 it will not be possible to detect the presence of truncated HER2 (CTFs). Also, in breast tumours where said CTFs of HER2 are expressed, antibodies such as trastuzumab are not therapeutic, since they do not recognise any epitope. This fact explains the resistance to the treatment with trastuzumab observed in patients expressing truncated forms (CTFs) of HER2.

Patients who express truncated forms or CTFs of HER2 should be treated with alternative therapies in order to prevent the poor prognosis numbers observed by Saez et al 2006 (supra). For the purpose of detecting (diagnosing) and treating as soon as possible people having tumours where HER2 truncated forms are expressed, it is very interesting to be able to distinguish what form of HER2 is expressed in order to act in consequence.

The document of Anido et al., "Biosynthesis of tumorigenic HER2 C-terminal fragments by alternative initiation of translation", *European Molecular Biology Organization (EMBO) Journal*—2006, Vol. 25, pp. 3234-3244, describes that in addition to the fragment generated by the action of the alpha-secretases on the HER2, which gives rise to a truncated form (CTF) known as P95 that includes the transmembrane and cytoplasmic fragment of the receptor, two truncated forms (CTF) are also generated through a mechanism of alternative initiation of translation starting from two methionines located upstream and downstream, respectively, of the transmembrane domain of HER2. Specifically, the methionines for the alternative initiation of translation correspond to methionine 611 and methionine 687 of the amino acid sequence with access number M11730.1 of the UniGene database of the National Center for Biotechnology Information (NCBI). This document also shows that these alternative forms of the HER2 receptor (CTFs) are present in breast tumours. In particular, it indicates that the most abundant corresponds to the form known as CTF687, or in other words, to the protein obtained by the alternative initiation of translation starting from the methionine in position 687. Anido et al. proposes as therapy the use of inhibitors of the tyrosin kinase activity of HER2, such as lapatinib, in order to minimise the growth of the tumours expressing these truncated forms of HER2. The inhibitors of tyrosin kinases act by interacting with the C-terminal end of the HER2 receptor that is present in an integral manner in both the complete receptor and in the CTFs derived from it or produced by alternative initiation of the translation.

The document of Scaltriti et al, "Expression of p95HER2, a truncated form of the HER2 Receptor, and response to anti-HER2 therapies in breast cancer", *Journal of National Cancer Institute*—2007, Vol. 99, pp. 628-368, represents an example of a study into an alternative methodology for detecting the presence of one of the HER2 receptor truncated forms and lists some of the possible causes of resistance to the treatment with trastuzumab (Herceptin). In particular, it emphasises the accumulation of the p95HER2 fragment (product of the proteolysis of HER2 by alpha-secretases) and other truncated forms of the receptor, which do not have the extracellular domain recognised by Trastuzumab. Scaltriti proposes a method of immunofluorescence to detect the p95HER2 fragment (product of proteolysis by alpha-secretases). This new detection method can be carried out on sections of tissue embedded in paraffin and fixed with formalin following clinical protocols. The new methodology arises from observing that the truncated form p95HER2, and not the entire form of the receptor, is located in both the plasmatic membrane and the cytoplasm of the cell. This method proposes comparing whether there is expression of p95HER2 by means of staining the detected cytoplasm with an anti-HER2 antibody that binds the receptor's cytoplasmic domain; and confirming these results with those of a detection with an anti-cytokeratin antibody, a protein whose distribution has been extensively used as a tool for the diagnosis of tumours. However, it is not clear whether this method efficiently distinguishes those tumours expressing the complete form of HER2 from those that express the truncated forms.

There is a need to locate new and efficient targets for diagnosis and therapy, properly correlated to the type of cancer in question and that make it possible to treat on time with efficient therapies those tumours having the worst prognosis, discarding from the outset those therapies that have been seen not to be effective.

The present invention offers benefits related to the problems cited above and represents a novel solution in the early classification of cancer, specifically breast cancer.

SUMMARY OF THE INVENTION

It has been determined that the presence of one of the truncated forms (CTF) of HER2, generated by the alternative initiation of translation, correlates very well with the prediction of the type of cancer to be treated, making easier the task of the physician at the moment of prescribing a course of treatment. This HER2 truncated form (CTF-611) has been identified and found to have the sequence SEQ ID NO:1.

This sequence has been used to develop several tools for detecting its presence in tissue samples, thus providing a new and solid diagnosis set that is also applicable in clinical routine.

The present invention also provides new antibodies, or fragments thereof, that recognise this truncated form or CTF of HER2, which is not recognised by trastuzumab. These antibodies recognize an epitope being defined by a sequence included in SEQ ID NO:2. The invention also provides hybridoma cell lines suitable for producing such antibodies. Anti-HER2 antibodies currently available recognize CTFs and HER2 or only HER2, making it very difficult to discriminate patients expressing only HER2 from patients expressing HER2 and CTFs. In contrast with available anti-HER2 antibodies, the antibodies described here preferentially bind to CTF-611, allowing to identify patients expressing this CTF.

The present invention also refers to a method of cancer diagnosis in patient samples which comprises the detection of the presence in said sample of the HER2 receptor truncated form consisting of SEQ ID NO: 1.

The present invention also provides the use of the antibody or fragment thereof of the present invention for the diagnosis and determination of prognosis in isolated samples of cancers where the HER2 receptor is expressed.

The present invention further provides an agent of diagnosis and determination of prognosis in isolated samples of cancers where the HER2 receptor and/or C-terminal fragments is expressed, which comprises at least one antibody or a fragment thereof as described above.

The present invention also provides a kit of diagnosis and determination of prognosis in isolated samples of cancers, where the HER2 receptor is expressed, that comprises means for detecting the presence in said sample of the HER2 receptor truncated form consisting of the SEQ ID NO: 1.

The invention also provides an antibody or a fragment thereof as described above for use in therapy or in the manufacture of a medicament. In particular, the medicament is for the treatment or prevention of cancers where at least the HER2 receptor truncated form consisting of the SEQ ID NO: 1 is expressed.

According to another feature of the invention, the use of antibodies or fragments is for the manufacture of a medicament for treating or preventing breast cancers in mammals, including human beings.

Another object of the present invention is a pharmaceutical composition for the treatment of cancers wherein at least the HER2 receptor truncated form consisting of SEQ ID NO: 1 is expressed, which comprises an antibody or a fragment thereof as described above and at least one pharmaceutically acceptable excipient and/or vehicle.

BRIEF DESCRIPTION OF THE DRAWINGS

FIG. 1: Diagram of the protein sequence of the truncated form CTF-611 (SEQ ID NO:1), compared with the sequence of the complete HER2 receptor (SEQ ID NO:6, depicting amino acids Asn571-Ser653 of HER2), and with the truncated form known as p95 (648-CTF/p95), (SEQ ID NO:7, depicting amino acids Ala648-Ser653), product of the proteolysis by alpha-secretases. The transmembrane domain is represented as a helicoidal line. The remaining molecule is indicted with a grey box. The sequence of the peptide used to generate mono and polyclonal antibodies appears underlined. The positions of intramolecular disulphide bridges are also indicated with connections between the cysteines.

(FIG. 3B). On the Y axis, N and V mean Number of Tumours and Volume of Tumours, respectively. On the X axis, T refers to Time in weeks.

FIG. 4A shows an electrophoresis and Western-Blot (transfer to membrane) revealed with an antibody (CB11) that recognises the cytoplasmic domain of the HER2 receptor (common domain in all complete and truncated forms) or with polyclonal antibodies generated against the peptide of SEQ ID NO: 3 (α-611-A and α-611-B). The tracks correspond to MCF7 cell lysate extracts (previously transformed with the constructions of FIG. 1) that express the complete form of the HER2 receptor, the CTF-611 truncated form and p95 truncated form. FIG. 4B shows the result of an immunoprecipitation test with the antibodies α-611-A, α-611-B and CB11 carried out on samples containing both the complete HER2 receptor as well as the truncated forms CTF-611 and p95.

FIG. 8(A): Graph showing the primary sequence of the juxtamembrane region of 611-CTF and the sequence of the different constructs used to map the epitopes—FIG. 8(B) Western blots.

FIG. 9(A) Table with analytical results. FIG. 9(B) immunocytochemical staining.

DETAILED DESCRIPTION

CTF-611

As previously mentioned, the inventors found that, surprisingly, the differential detection of said HER2 truncated form with SEQ ID NO: 1 correlates very well with the manifestation of a common type of cancer in breast tissue with a poor prognosis. Thus, FIG. 3 shows the results of the evaluation of the number of tumours developed in transgenic mice expressing the truncated form CTF-611 (SEQ ID NO: 1).

Figure 3:
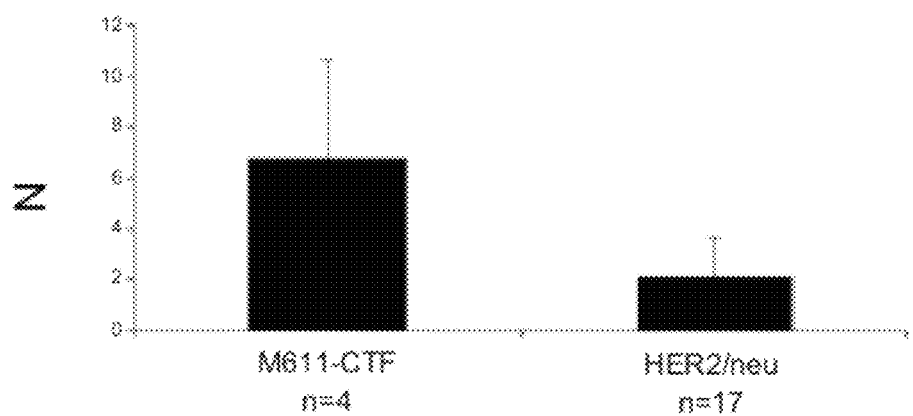
FIG. 3: Results of the evaluation of the number of tumours developed in transgenic mice that express the truncated CTF-611 (FIG. 3A) form in comparison with transgenic mice that express the complete HER2 receptor; and the results of the volume of detected tumours.
Figure 3:
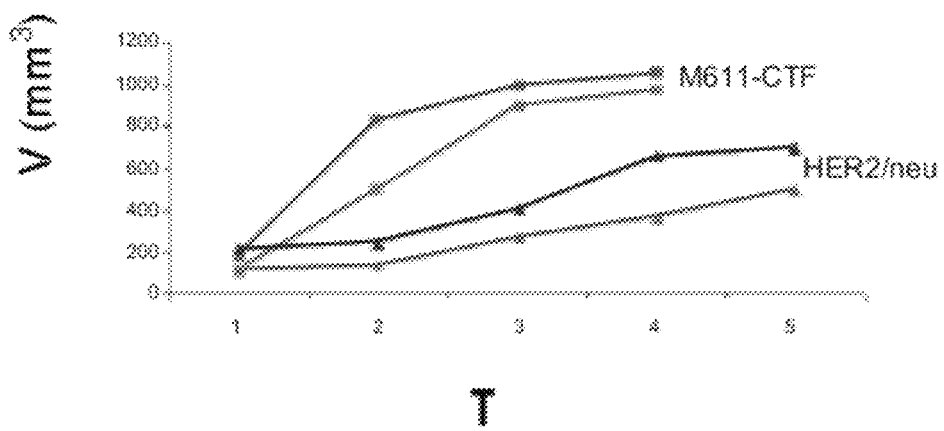

In order to obtain the results of this FIG. 3, cDNA constructs were expressed in the breast epithelium of mice, said constructs coding the human SEQ ID NO: 1 (CTF-611), identified in the figure as M611-CTF. This construct comprises the SEQ ID NO: 1 under control of the promoter of the mouse mammary tumour virus (MMTV). As control the mouse line FVB/N-Tg(MMTVneu)202J that expresses the complete form of HER2 was used, also under control of the MMTV promoter. As can be deduced from FIG. 3A, the number of tumours in mice expressing the cDNA construct with the CTF-611 form (SEQ ID NO: 1) is much higher than the one of the FVB/N-Tg(MMTVneu)202J line, identified in this figure with the designation HER2/neu. The tumours in the transgenic animals were detected at 17 weeks of age of the transgenic animals expressing CTF-611, which represents three months before the first detection in FVB/N-Tg(MMTVneu)202J mice. This fact would explain the greater aggressiveness of tumours that express HER2 fragments in relation to those tumours that express the complete form. FIG. 3B also shows that the volume of the tumours is much greater in the animals expressing the CTF truncated form of HER2 with SEQ ID NO: 1, in relation to those animals expressing constitutively the whole receptor, also known as HER2/neu. This second fact also explains the greater aggressiveness of this type of tumours. The inventors also determined that those tumours expressing the truncated form of sequence SEQ ID NO: 1 showed higher lung metastasis indices than those observed in the tumours expressing HER2/neu. Further experiments proving the clinical relevance are provided in Example 9 below.

All of this data with transgenic animals reveals that the differential detection of the HER2 receptor truncated form of SEQ ID NO: 1 in respect of the complete form of the receptor is very necessary.

Evidently, said SEQ ID NO: 1 includes all variants derived from allelic variations between individuals, which entail variations in number and type, of some amino acids, such as more or less than two or three amino acids, or the replacement of an amino acid by another one which does not modify the overall receptor's structure.

These truncated forms of HER2 can contain neo-epitopes, in other words, new antigenic determinants not present in the molecule of the whole receptor, meaning that they do not interact in the same way with the molecules as with the whole receptor (antibodies, medicaments, etc.).

Antibodies to CTF-611

The inventors could produce both polyclonal and monoclonal antibodies to CTF-611. These antibodies recognize an epitope that is defined by a sequence included in SEQ. ID NO: 2, preferably by a sequence included in or defined by SEQ. ID NO: 3. Most preferred are antibodies that recognize an epitope that is included in or defined by MPIWKFPDEEGAS (SEQ. ID NO: 5).

In the context of the present invention, epitope is understood to mean the part of a peptidic type macromolecule (or of an antigen), whose sequence and/or spatial configuration is recognised by the immune system (antibodies, T cells, B cells).

The antibodies of the present invention can preferably distinguish the protein of SEQ ID NO:1 from the HER2 receptor. Furthermore, the antibodies of the present invention can preferably distinguish the protein of SEQ ID NO:1 from the HER2 receptor truncated form 648-CTF/p95. This distinction can be visualized by one or more of immunofluorescence, flow cytometry, immunohistochemistry in cultured cells, and immunohistochemistry in samples from patients. It is particularly preferred that the distinction can be quantified both in flow cytometry and immunoprecipitation.

According to the present invention, the binding of the antibodies of the present invention to 611-CTF is preferably at least 300 times, more preferably at least 1000 times, most preferably 1000 to 2000 times stronger than their binding to HER2 in an immunoprecipitation experiment, as described in more detail in Example 3 (using 5 microgram of 32H2 and 5 microgram of 20F4).

As noted above, the antibody can be polyclonal or monoclonal.

In the sense of the present invention, "polyclonal antibody" shall be understood to mean the group of antibodies produced by different B cell lines (B lymphocytes). Polyclonal antibodies are mixtures of immunoglobulins secreted against an antigen (macromolecule), each one of these immunoglobulins being capable of recognising a different epitope, since it comes from a different B cell. Thus, within the different populations of immunoglobulins contained in a polyclonal antibody, there is a type of immunoglobulin that recognises the epitope or epitopes of interest of a specific antigen.

Polyclonal antibodies can be produced for example by conjugating the peptide of SEQ ID NO. 2, SEQ ID NO. 3, SEQ ID NO: 4 or SEQ ID NO: 5 with an immunogen such as Keyhole-limpet hemocyanin and immunising rabbits with this conjugate.

Monoclonal antibodies can be produced using the same or similar immunogens. Hybridoma cell lines can be produced in a manner known to the skilled person. The hybridoma cell line can then be grown in a suitable culture medium from which the monoclonal antibody is recovered.

In a preferred embodiment, they are produced by the hybridoma cell line deposited with the "Deutschland Sammlung von Mikroorganismen and Zellkulturen GmbH—DSMZ" with access number DSM ACC2904, deposited in accordance with the Treaty of Budapest on 9 Apr. 2008 or the hybridoma cell line deposited with the "Deutschland Sammlung von Mikroorganismen und Zellkulturen GmbH—DSMZ" with access number DSM ACC2980, deposited in accordance with the Treaty of Budapest on 6 Nov. 2008. The DSMZ—Deutschland Sammlung von Mikroorganismen und Zellkulturen GmbH, Inhoffenstr. 7B, D-38124, Braunschweig, Germany.

Monoclonal antibodies produced with these hybridoma cell lines, as well as monoclonal antibodies that are functionally at least equivalent are particularly preferred. Functionally at least equivalent are those antibodies that can discriminate between CTF-611 and HER2 equally well or even better.

Useful antibodies also include humanized and human antibodies.

The present invention thus also provides the isolated peptides of sequence SEQ ID NO. 2, SEQ ID NO. 3, SEQ ID NO: 4 or SEQ ID NO: 5.

Instead of the complete antibody, a fragment thereof may be used according to the present invention. The antibody fragments are selected from the group comprised by F(ab), F(ab') and Fv. In the context of the present invention, a fragment of an antibody refers to a part of the antibody which is of enough size and appropriate structure to bind to an epitope present in the HER2 receptor truncated form and thus permit its detection in a sample.

Examples 2 and 3 show specific antibodies. Evidently, the invention extends to other polyclonal or monoclonal antibodies directed against the epitope of the CTF-611 truncated form which is defined by the sequences SEQ ID NO: 2 and SEQ ID NO: 3, since, on the basis of the teachings of this invention they can be directly derived for a skilled in the art. Equally, the invention extends to fragments of said antibodies, such as F(ab), F(ab'), Fv, etc., or any hybridoma cell line capable of producing monoclonal antibodies directed against the peptides of SEQ ID NO:2 and SEQ ID NO: 3.

Diagnostic Methods

In the method of diagnosis according to the invention the detection of the presence of the HER2 receptor truncated form may be carried out through means independently selected from the group comprised by: detection by differential migration in a mobile phase—stationary phase system of the HER2 receptor truncated form consisting of SEQ ID NO: 1 in respect of the complete form of said HER2 receptor; and detection by binding with specific antibodies of the HER2 receptor truncated form containing the SEQ ID NO: 1.

Detection through differential migration should be understood to mean, in the context of the present invention, any analytical technique that allows separation of the compounds to be detected on the basis of their different mobility in a specific mobile phase—stationary phase system, such as an electrophoresis. Such different mobility may be caused by a different electrical charge in the compound, different molecular weight, or different affinity for other compounds.

This differential detection can be carried out through analytical techniques known by the skilled in the art such as protein electrophoresis, molecular exclusion chromatographies, antibody affinity tests, immunofluorescence, immunocytochemistry, immunohistochemistry, flow cytometry, etc. Particularly preferred is immunohistochemistry. One or more of these methods can be combined to enhance reliability.

Differential detection of the HER2 receptor truncated form consisting of SEQ ID NO: 1, also referred to in this invention as CTF-611, in respect of the whole or complete HER2 receptor, implies being able to visualise two proteins with different molecular weights and different sequences as can be desired from FIG. 1. The truncated form with SEQ ID NO: 1 consists of the protein resulting from the alternative initiation of translation through methionine 611 of the complete sequence of the HER2 receptor. This form or CTF thus comprises a new extracellular domain, a transmembrane fragment, and a cytosolic domain. The transmembrane fragment and the cytosolic domain are the same as those of the complete form of the HER2 receptor. Another truncated form corresponds to the one of FIG. 1 referred to as p95 or CTF-648. This last form is the product of the action of the alpha-secretases on the complete HER2 receptor, which divide a large part of the extracellular domain.

According to another embodiment of the invention, the step of detecting the presence in the sample of the HER2 receptor truncated form consisting of SEQ ID NO: 1, comprises the detection with at least one antibody as defined above. In a particular embodiment, the method of diagnosis according to the invention comprises the detection of the epitope defined by SEQ ID NO: 3.

In one embodiment of the invention, the antibodies or fragments thereof of the present invention are used as agents for the diagnosis and determination of prognosis, either directly marked in their own peptidic sequence (for example with radioisotopes) or indirectly (for example by addition or binding a fluorescent agent or an agent capable of producing fluorescence by reaction in a selected reaction medium), all of the above with the aim of generating a visible signal, and if possible quantifiable, with which to detect the presence of the HER2 receptor truncated form consisting of the sequence SEQ ID NO: 1 in a sample.

In the same way, it is contemplated for the diagnosis agent containing at least the antibodies to be adhered to a solid support, directly or indirectly by means of a spacer arm. An agent of this type allows capturing of the form of sequence SEQ ID NO: 1 of a sample, in order to determine its presence afterwards with other non-specific antibodies (such as CB11).

The agents of diagnosis and determination of prognosis according to the invention can also be applied in immunohistochemistry protocols. To this effect, the (primary or secondary) monoclonal or polyclonal antibodies must be duly marked to give a visible signal, and in the best of cases quantifiable, once they have come into contact with the tested tissue and they have been allowed to interact with the proteins intended for detection, in other words, with the CTF fragment of HER2 of sequence SEQ ID NO: 1.

With the aim of facilitating the task of analysis, diagnosis and determination of the prognosis to the physician, it is contemplated that the diagnostic agent is provided in the form of a kit which includes, besides the antibodies, the reagents (e.g. reagents required for the immunohistochemical staining), buffers and detection solutions adapted to determine the presence of the truncated form of SEQ ID NO: 1 in a sample, possibly control slides representing different expression levels of CTF-611 and possibly also detailed instructions, assisting the physician in the assessment of the diagnosis. This kit may also comprise a means for carrying out a semi-quantitative immunohistochemical assay for the determination of HER2 (such as Herceptest™).

Thus, the invention provides a kit for diagnosis and determination of the prognosis, which comprises at least one antibody or a fragment thereof, said antibody or fragment being capable of recognising the epitope defined by SEQ ID NO:2 or SEQ ID NO: 3 or SEQ ID NO:5, in addition to the reagent means and buffers suitable for carrying out the interaction of the antibody with the epitope and that are extensively known by those skilled in the art.

The diagnostic method of the present invention, and the kit of the present invention, may allow the prediction of nodal metastasis, poor prognosis, and resistance to Herceptin™.

Another type of kit also object of the invention, comprises all the necessary means for carrying out detection through differential migration of the HER2 receptor truncated form consisting of the sequence SEQ ID NO: 1, in relation to the complete form of the HER2 receptor.

Within the group of cancers that express the HER2 receptor or its truncated variants, breast cancer stands out. Other cancers where these proteins are also expressed include the cancer of lung, pancreas, colon, stomach, prostate, head and neck, skin, kidney, testicle, thyroids, urinary bladder, uterus, vulva, endometrial, ovary, oesophagus, mouth, salivary gland, larynx, peritoneum, nose and throat region, Fallopian tubes, Wilms tumors as well as lymphomas, Swing sarcomas, synovial sarcoma, medulloblastomas, trophoblastic tumors, glyomas, glyoblastomas, cholangiocarcinomas, cholesteatoma, chondrosarcoma, ependymoma, neurilemmomas, neuromas, rhabdomyosarcomas. The diagnostic method of the present invention is thus particularly suitable for diagnosing one of these cancers. In addition to ex-vivo detection of-CTFs the antibodies could be used for in vivo imaging.

Therapeutic Methods

The antibodies of the present invention, or fragments thereof, are also useful in therapy, particularly in the therapy of cancer, particularly those cancers that express the HER2 receptor or its truncated variants. Humanized and human antibodies, and fragments thereof, are preferred.

The antibodies of this invention are used also in pharmaceutical compositions useful for the treatment of cancers in which at least the HER2 receptor truncated form consisting of SEQ ID NO: 1 is expressed. The composition comprises those pharmaceutically acceptable vehicles or excipients and at least one antibody that recognises the epitope defined by the sequences SEQ ID NO: 2 or SEQ ID NO: 3. The pharmaceutical composition may also comprise a mixture of antibodies that, besides an antibody of the present invention, contains other antibodies against HER2 or fragments thereof, such as Herceptin™.

Based on the figures provided herein and always by way of illustrative but not limiting examples, below there are described the method of diagnosis and determination of prognosis of cancers where the HER2 receptor and/or its carboxy terminals fragments (truncated variants) are expressed; new peptides and specific antibodies against said peptides; new cell lines; diagnosis agents and kits for detection, all of which being objects of the invention.

Although not specified, all technical and scientific terms used in the specification have the meaning that a skilled in the art, to who the invention belongs, would assign to them. Similar or equivalent methods and materials to those described herein may be used in the practice of the present invention. Throughout the description and claims the word "comprise" and variations of the word, such as "comprising", is not intended to exclude other technical features, additives, components, or steps. Additional objects, advantages and features of the invention will become apparent to those skilled in the art upon examination of the description or may be learned by practice of the invention. The following examples and drawings are provided by way of illustration, and are not intended to be limiting of the present invention.

Also, it shall be understood that the present invention covers all possible combinations of preferred and particular groups described above.

EXAMPLES

The following examples show different ways of detecting the presence of the truncated form of sequence SEQ ID NO: 1, in an isolated sample of cancer of the type that expresses the HER2 receptor and/or its truncated variants.

Experimental Procedures

Cells. MCF7 Tet-Off cells (BD bioscience) were maintained at 37° C. and 5% CO2 in DMEM/F-12 (1:1) (Gibco) containing 10% FBS (Gibco), 4 mM L-Glutamine (PAA Laboratories), 0.2 mg/ml G418 (Gibco) and 1 µg/ml doxycycline (Sigma). Cells were transfected with the various expression plasmids by using FuGEN6 (Roche). Single stable clones with pUHD10-3 h based plasmids integrated were selected with 0.1 mg/ml hygromycin B (Invitrogen). Expression from pUHD10-3 h encoded cDNAs of HER2 and CTFs was induced by removing doxycycline. First the cells were detached with 0.5% Trypsin-EDTA (GIBCO), washed three time by centrifugation and the medium changed 10 hours after seeding in culture dishes. Homogeneity of the individual clones was checked by immunofluorescence confocal microscopy with an antibody against the cytoplasmic domain of HER2. Two independently selected stable clones were used in the experiments.

Western Blot. Cells expressing the different HER2 isoforms were lysed in modified RIPA buffer (20 mM NaH2PO4/NaOH pH7.4, 150 mM NaCl, 1% Triton X-100, 5 mM EDTA, 100 mM PMSF, 25 mM NaF, 16 µg/ml Aprotinin, 10 µg/ml Leupeptin and 1.3 mM Na3VO4) and protein concentrations determined with DC protein assay reagents (BIO-RAD). Samples were mixed with loading buffer (final concentrations: 62 mM Tris pH6.8, 12% glycerol, 2.5% SDS) with 5% betaMercaptoethanol and incubated at 99° C. for 5 min before fractionation of 15 µg protein by SDS-PAGE. Specific signals in Western blots were quantified with the software ImageJ 1.38 (NIH).

Immunoprecipitation. Cell lysates were incubated with different antibodies during 1 hour at 4° C. Then, immunocomplexes were purified with protein A. Immunoprecipitates were washed three times with lysis buffer, mixed with loading buffer and analyzed by Western blot.

Cells for immunofluorescence microscopy seeded on glass cover-slips were washed with PBS, fixed with 4% paraformaldehyde for 20 min and permeabilized with 0.2% Triton X-100 for 10 min. For blocking and antibody binding we used PBS with 1% BSA, 0.1% Saponin and 0.02% NaN3, and for mounting Vectashield with DAPI (Vector laboratories).

Flow Cytometry. MCF7 cells expressing HER2, 611-CTF or 648- were washed at 4° C. with PBS and detached in PBS containing 5 mM of EDTA. Detached cells were Incubated with 10 µg/ml of anti-32H2 monoclonal antibody in PBS containing 5% BSA for 30 min at 4° C. washed and stained for 30 rain at 4° C. with FITC-conjugated anti-mouse IgG (Becton-Dickinson) in PBS containing 5% BSA. Flow cytometry was done on a FACscan using FACscan Research software (Becton Dickinson Immunocytometry Sys., Mountain View, Calif.).

Immunohistochemistry. MCF7 cells expressing HER2, 611-CTF or 648- were washed at 4° C. with PBS and detached in PBS containing 5 mM of EDTA. Then, cells were centrifuged and cell pellets were fixed in 10% neutral formalin, dehydrated and embedded in paraffin. Sections from cell pellets or from human tissues of a thickness of 4 μm were placed on poly-lysine-coated glass slides. Immunohistochemistry analyses were performed using the following protocol:

1. Deparaffinizing and rehydrating the section
1.1 Incubate the slides 30 min at 60° C.
1.2 Deparaffinize the slides with three 5 min. incubations of clean xylene, followed by two 3 min washes with absolute ethanol.
1.3 Gradually bring to distilled water: Ethanol 95° C. 3 min, Ethanol 70° C. 3 min, Ethanol 50° C. 3 min, distilled water.
2. Antigen retrieval
PT Link at low PH (6), ENVISION FLEX TARGET RETRIEVAL SOLUTION HIGH Ph 10×. DM 812.20 min a 95° C.
Wash with Envision Flex wash buffer ×10 DM 811 15 min.
3. Immunohistochemical staining
AUTOSTAINER plus Link DAKO
KIT: ENVISION FLEX+MOUSE, High Ph (Link):
Envision Flex Peroxidase Blocking SM801.
Envision Flex/HRP SM 802.
Envision Flex DAB+CHROMOGEN DM 807.
Envision Flex Substrate Buffer SM 803.
Envision Flex Wash Buffer 10×DM 811.
Envision Flex Target Retrieval Solution High Ph 10×DM 812.
Envision Flex+Mouse (linker) SM 84.
Peroxidase 5 min and wash with washing buffer.
Protein Block 5% 15-20 min.
Wash with washing buffer.
    32H2 diluted 1: 1000-1:3000 (1 mg/ml stock) or 20F4 diluted 1:20-1:50 (1 mg/ml stock) 2 hours.
    Wash with washing buffer.
    Secondary (Flex HRP, Flex+Mouse/Rabbit) 20 min.
    Wash with washing buffer.
    DAB 5 min.
    Wash with wash buffer.
    Hematoxylin.
    Wash with distilled water.
3. Dehydrating and stabilizing with mounting medium
3.1 Gradually wash with increasing concentrations of ethanol (50%, 70%, 95%, 2 min each wash).
3.2 Gradually bring to distilled water (ethanol 95%, 70%, 50%, distilled water, 3 min each wash).
3.3 Wash with Xylene/eucalyptol (3 washes 2 min each).
3.4 Mount with DPX.

Transgenic Mice

TG 611 and TG 687 mice were engineered by cloning the sequences encoding 687-CTF and 611-CTF into the multiple cloning site II downstream of the Rous sarcoma virus enhanced mouse mammary tumor virus long terminal repeat of the pMB vector (a kind gift from Dr. Marcos Malumbres, CNIO, Madrid). Founder lines were generated by microinjecting linearized plasmid DNA into fertilized oozytes harvested from superovulated FVB mice in the Centre of Animal Biotechnology and Gene Therapy (Centre de Biotecnologia Animal i Teràpia Gènica, Universitat Autònoma de Barcelona). Founder mice were genotyped by Southern hybridization analysis. After identification of founder animals, routine colony maintenance was performed by PCR genotyping. The male and female FVB/N-Tg(MMTVneu)202J mice were obtained from the Jackson Laboratory (Bar Harbor, Me.).

Whole Mounts and Histology

Mammary glands were mounted on glass slides, fixed overnight in 4% paraformaldehyde and transferred to 70% ethanol. The slides were rinsed in water for 5 min and stained in a filtered solution of 0.2% carmine for 24 hours. Glands were then dehydrated sequentially with decreasing concentrations of ethanol, then defatted and stored in methyl salicylate. For histological analysis, fixed glands were blocked in paraffin, sectioned, and stained with hematoxylin and eosin.

Example 1

Detection of the Fragment of SEQ ID NO: 1 Through Differential Migration

Figure 2:
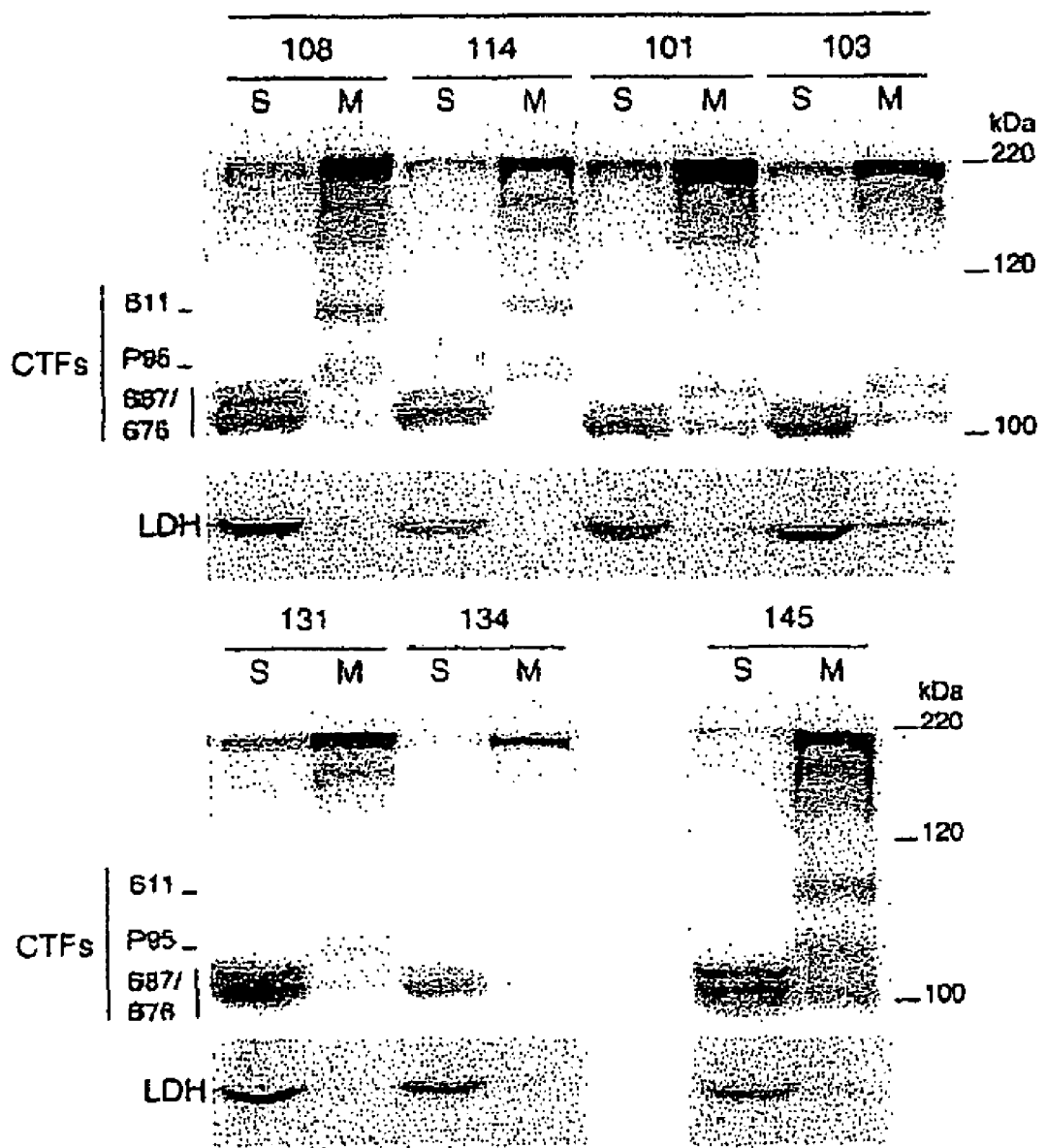
FIG. 2: Electrophoresis and Western-blot (transfer to membrane) of breast cancer samples. (S) means soluble fraction and (M) membrane fraction. In order to detect complete HER2 and the CTF-611 form, antibodies directed to the cytoplasmic domain of the proteins were used. DHL: Lacatate dehydrogenase (used as control).

In FIG. 2, which corresponds to an image of an electrophoresis gel and subsequent Western-type transfer (Western-blot), different samples of breast cancer (108, 114, 101, 103, 131, 134 and 145) were loaded on the tracks. From each sample both the soluble fraction (S) and the membrane fraction (M) of the cell lysate were analysed, in order to visualise what type of HER2 molecule was present and in what fractions. In principle, it is expected that both the complete receptor and the form of the SEQ ID NO: 1 are in the cell membrane. For the detection of complete HER2 and of CTF-611 form, antibodies were used (CB11) directed to the cytoplasmic domain of the proteins, which is a common domain in both protein forms. As an analysis' control the presence of the lactate dehydrogenase (DHL) enzyme was detected. In most samples, bands corresponding to the complete HER2 receptor and in the membrane fraction, a band corresponding to form CTF-611 of SEQ ID NO: 1 appears.

FIG. 2 therefore shows that detection of the type of truncated forms of the HER2 receptor can be carried out through a protein electrophoresis analysis. Furthermore, the presence of a fragment of HER2 of sequence SEQ ID NO: 1 is indicative of a certain type of cancer, in the case of the example, breast cancer, which needs to be evaluated and treated as an individual case within the cancers that express HER2.

Example 2

Detection of the Presence of the HER2 Fragment of Sequence SEQ ID NO: 1 with Polyclonal Antibodies Directed to Neo-Epitopes Defined by the SEQ ID NO: 2 or SEQ ID NO: 3

With the aim of being able to detect the presence of the HER2 truncated form, whose sequence is the one described in SEQ ID NO: 1, using alternative means to those of detection through differential migration in electrophoresis, a peptide having the sequence SEQ ID NO: 4 was synthesized and four rabbits were immunised with said peptide. This peptide corresponds to the 32 amino acids of the N-terminal end of the CTF-611 form or of SEQ ID NO:1, in which most cysteines have been replaced by serines for the purpose of conjugating it with the immunogen known as Keyhole-limpet hemocyanin (KLH).

SEQ ID NO: 4 corresponds therefore to a peptide equivalent to that of SEQ ID NO: 3, although adapted in order to carry out the immunisation technique. A skilled in the art will understand that the antibodies directed against the synthesized peptide SEQ ID NO: 4 will also recognise the epitope defined by the SEQ ID NO: 3 present in the truncated form of the HER2 receptor (SEQ ID NO: 1 or CTF-611). Similarly, a skilled in the art can follow that if the synthesized peptide used for immunisation consists of SEQ ID NO: 2, which comprises all of the amino acids of the CTF-611 receptor located in the extracellular zone, the results with antibodies directed against this other peptide are equivalent and therefore useful for the same purpose.

A SDS electrophoresis and subsequent Western transfer of MCF7 cell lysate extracts (previously transformed with the constructs of FIG. 1), expressing the complete form of the HER2 receptor, the CTF-611 truncated form and the p95 truncated form were carried out. The truncated form of SEQ ID NO: 1 appeared in fact as two fragments of similar molecular weight. As can be derived from tests performed with Glycosidase-F, an enzyme that eliminates N-glycans from proteins (not shown), the fragment CTF-611 is a substrate of post-translational modifications. Specifically, a fragment with approximately 110 kDa corresponds to the form that is synthesized and subsequently enters into the secretary route, where it becomes N-glycosylated.

Figure 4:
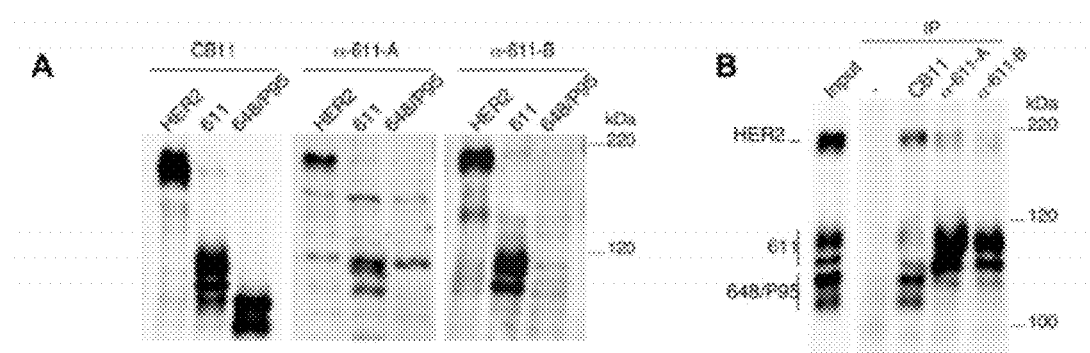
FIG. 4.

The serum of two of the immunised rabbits recognised both the complete HER2 receptor, and CTF-611. This can be seen from FIG. 4A, where the bands corresponding to both the complete HER2 receptor and the form of SEQ ID NO: 1 or CTF-611 are detected. As indicated in said FIG. 4A, the Western blot was revealed with an antibody (CB11) that recognises the cytoplasmic domain of the HER2 receptor (domain common in all forms, complete and truncated); or with the polyclonal antibodies generated against said peptide of SEQ ID NO: 4 (α-611-A and α-611-B) and that are present in the serums of rabbits. Because it is comparable to the signal of complete HER2 and CTF-611, it is concluded that the antibodies α-611-A and α-611-B recognise a linear epitope that is present in both forms of the receptor. As a negative control in the SDS electrophoresis and Western blot a MCF7 cell lysate, expressing the receptor form known as p95, which does not possess the epitope against which the antibodies had been designed, was used.

In contrast to these results, when an immunoprecipitation assay was carried out with the antibodies α-611-A and α-611-B and the antibody CB11, it was detected that the antibodies directed against the peptide of SEQ ID NO: 4 precipitated preferably the truncated form of the receptor (CTF-611). The mixture that was subjected to immunoprecipitation contained a proportion of 1:1:1 of the cell lysates that expressed the different forms of the HER2 receptor. These results are evident in FIG. 4B. In this figure, the bands from a SDS electrophoresis and subsequent Western transfer appear, on the tracks of which the results of the immunoprecipitation assays with the antibodies α-611-A, α-611-B and CB11 were loaded. A control track (input) was loaded with the mixture 1:1:1 of the three types of cell lysates subjected to immunoprecipitation with the different antibodies. The Western blot was revealed with CB11. (Approx. 106 cells expressing full-length HER2, 611-CTF or 648-CTF were lysed in 500 μl of lysis buffer (50 mM Tris HCL pH7.4, 137 mM NaCl, 2 mM EDTA, 10% Glycerol, 1% NP40). Lysates were clarified by centrifugation at 14000 g×30 min. Input: 5 μl lysate mix (Full length HER2:CTF611:CTF648, 1:1:1)
IP: 50 μl lysate mix+5 μl anti 611CTF serum from rabbit or CB11

In the tracks corresponding to the immunoprecipitation with the antibodies α-611-A and α-611-B, there can be distinguished bands that are clearly more intense than the rest; in those molecular weights corresponding to the glycosylated and non-glycosylated form of CTF-611. That is, said antibodies directed against the peptide of SEQ ID NO: 4 do not immunoprecipitate the complete form of the HER2 receptor, which means that they really recognise an epitope which is masked when the complete HER2 receptor is not denaturalised. Therefore, it can be concluded that the antibodies α-611-A and α-611-B are specific for CTF-611.

This specificity is corroborated by indirect immunofluorescence assays (not shown) in which the affinity purified polyclonal antibodies α-611-A and α-611-B only allow the staining in samples expressing the truncated fragment CTF-611. This fact involves the advantage of making it possible to use them to detect differentially what form of the HER2 receptor is expressed in an isolated sample of tumour tissue. Affinity purification of the polyclonal antibodies was performed as follows:
(i) Total IgG purification using a HiTrap Protein A HP column (GE Healthcare). Antibodies from rabbit serum were immobilized into the column equilibrated with binding buffer (Na2HPO4), washed with 10 column volumes of binding buffer and eluted in 10 volumes of citric acid ph (2.7). The elution was neutralized using Tris-HCL pH 8.
(ii) Purification using a peptide immobilized in a HiTrap NHS column. The same peptide used to immunize the rabbit was immobilized into a HiTrap NHS column. IgGs purified in the previous step were loaded into the column equilibrated with binding buffer (Na2HPO4), washed with 10 column volumes of binding buffer and eluted in 10 volumes of citric acid ph (2.7). The elution was neutralized using Tris-HCL pH 8.
(iii) Finally the purified antibody was dialyzed against PBS 0.02% NaN3.

The complete HER2 receptor comprises, close to the cell membrane, a structured region maintained by six disulphide bridges, indicated in FIG. 1 by connection lines between cysteines. The truncated form CTF-611, or of sequence SEQ ID NO: 1, contains only five cysteines among which said disulphide bridges are established to stabilise the homodimers of this truncated form. As can be derived from FIG. 4 as a whole, one must conclude that the zone close to the cell membrane of the truncated form of SEQ ID NO: 1 is antigenically different from its equivalent in the complete HER2 receptor. From this, it is derived that it can be detected differentially according to what has been previously indicated.

Quantification of the different HER2 isoforms in the input, CB11 and anti-611-B immunprecipitates normalized to the amount of HER2 shows are as follows:

|  | Input | CB11 | Anti-611-B |
|---|---|---|---|
| HER2 | 1 | 1 | 1 |
| 611-CTF | 1.47 | 1.27 | 23.20 |
| 648-CTF | 1.53 | 2.76 | 2.4 |

The quantification was carried out using ImageJ 1.38.

Example 3

Detection of the Presence of the HER2 Fragment of Sequence SEQ ID NO: 1 with Monoclonal Antibodies Directed at Neo-Epitopes Defined by SEQ ID NO: 2 or SEQ ID NO: 3

Figure 5:
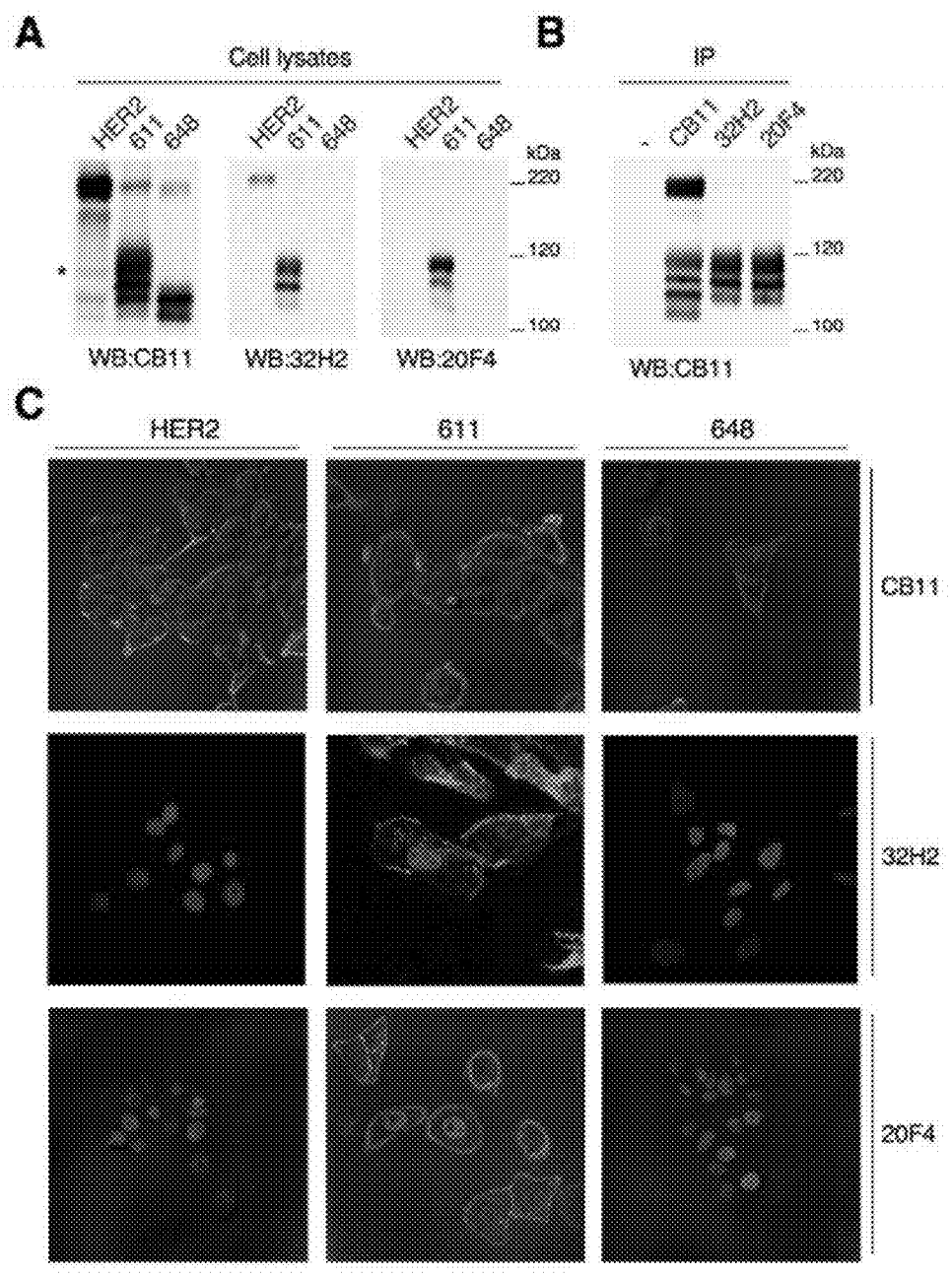
FIG. 5: (A) MCF7 cells expressing HER2, 611-CTF or 648-CTF were lysed and analyzed by Western blot with CB11, an antibody against the cytoplasmic domain of HER2, or with two independent monoclonal anti-611-CTF antibodies raised against the peptide MPIWKFPDEEGASQPSPIN-STHSSVDLDDKGC (SEQ ID NO: 4; see FIG. 1). (B) The lysates from MCF7 cells expressing HER2, 611-CTF or 648-CTF were mixed 1:1:1 and subjected to immunoprecipitation with the indicated monoclonal antibodies. As a negative control a mock immunoprecipitation with no antibody (−) was performed. (C) MCF7 cells expressing HER2, 611-CTF or 648-CTF were analyzed in a confocal microscope by indirect immunofluorescence with the indicated antibodies.

Using the same peptide of SEQ ID NO: 4 of example 2, monoclonal antibodies were obtained. From all of them, monoclonal antibody 20F4 produced by the hybridoma cell line with access number DSM ACC2904 and monoclonal antibody 32H2 produced by the hybridoma cell line with access number DSM ACC2980 were selected. The results obtained with this antibody are shown in FIG. 5.

In a similar way as in example 2, it was carried out a SDS electrophoresis and the subsequent Western transfer with a 1:1:1 mixture of MCF7 cell lysate extracts (previously transformed with the constructs of FIG. 1), that expressed the HER2 receptor complete form, or the CTF-611 truncated form, or p95 the truncated form. In FIG. 5A, which is a photograph of the membrane of the Western revealed with CB11 or with the monoclonal antibodies 20F4 and 32H2, one can see that the latter recognise specifically the truncated form of HER2 corresponding to the receptor CTF-611 of SEQ ID NO: 1 and does not present any detectable cross-reactivity with the complete form of said receptor, which means that it really recognises a new epitope (neo-epitope) that includes the primary amino group on the N-terminal end of the CTF-611 form of the receptor.

In a similar way, when an immunoprecipitation assay was carried out with the monoclonal antibodies 20F4 and 32H2 in comparison with the antibody CB11 (which recognises the cytosolic domain of the receptors), it was detected that the monoclonal antibody directed against the peptide of SEQ ID NO: 3 precipitated exclusively the truncated form of the receptor (CTF-611). These results are evident in FIG. 5B. In this figure, there are shown the results of a SDS electrophoresis and the subsequent Western transfer, on the tracks of which the results of the immunoprecipitation assays with the antibodies 20F4, 32H2 and CB11 were loaded.

On the track corresponding to immunoprecipitation with the antibodies 20F4 and 32H2, only the bands of the glycosylated and non-glycosylated form of the CTF-611 truncated form can be distinguished. That is, antibodies 20F4 and 32H2 do not immunoprecipitate the complete form of the HER2 receptor. Therefore, it can be concluded that the antibodies 20F4 and 32H2 are highly specific to CTF-611 and do not recognise the complete form of HER2, meaning that it can be used for the differential and highly selective detection of what form of the HER2 receptor is expressed in an isolated sample of tumour tissue.

The characterization of monoclonal antibodies directed against a peptide corresponding to a the N-terminal, 32 amino acid-long, sequence of 611-CTF, confirm the existence of epitope(s) masked in full-length HER2 but exposed in 611-CTF. These epitopes are masked both in the solubilized molecule and in intact cells. Quantification of the different HER2 isoforms in the CB11, 32H2 and 20F4 immunprecipitates normalized to the amount of HER2 shows are as follows:

|         | CB11 | 32H2   | 20F4    |
|---------|------|--------|---------|
| HER2    | 1    | 1      | 1       |
| 611-CTF | 1.01 | 343.50 | 1302.19 |
| 648-CTF | 0.79 | nd     | nd      |

Example 4

Figure 6:
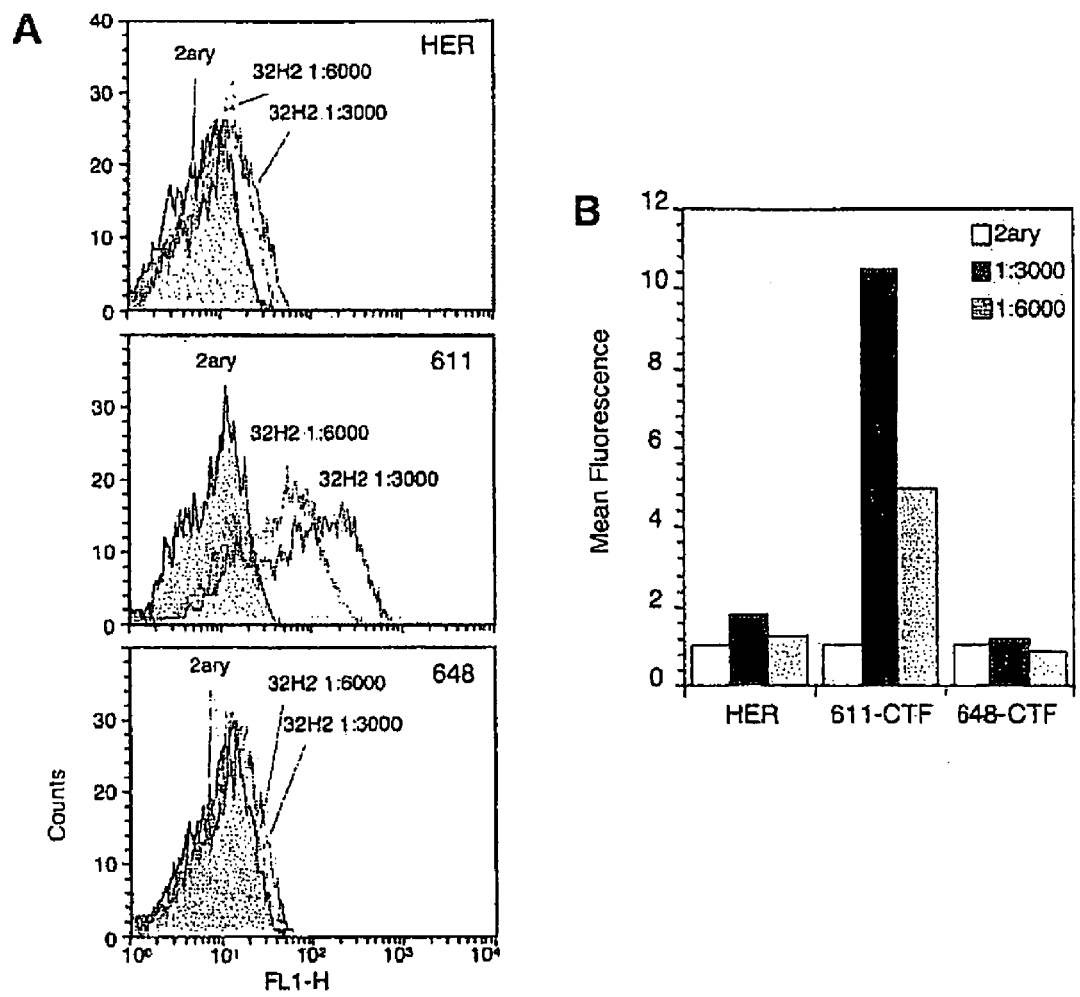
FIGS. 6 (A) and (B): Characterization of one monoclonal antibody by flow cytometry

Characterization of One Monoclonal Antibody Against the N-Terminus of 611-CTF by Flow Cytometry (A) MCF7 cells expressing HER2, 611-CTF or 648-CTF were analyzed by flow cytometry using different concentrations of 32H2, a monoclonal antibody raised against the peptide MPIWKFPDEEGASQPSPINSTHSSVDLDDKGC (SEQ ID NO: 4; see FIG. 1). See FIG. 6(A).

(B) The results of two independent experiments performed as in (A) were quantified and the average are shown. See FIG. 6(B).

(C) MCF7 cells expressing HER2, 611-CTF or 648-CTF were analyzed in a confocal microscope by indirect immunofluorescence with the indicated antibodies.

As fluorophore-coupled secondary antibody, Alexa Fluor 488 goat-anti mouse IgG from Invitrogen (A110011) was used. To assess unspecific binding as a negative control, FACS was carried out without 32H2 serum but in the presence of this secondary antibody ("2ary").

Conclusion: The epitope recognized by the antibody 32H2 is exposed in live cells expressing 611-CTF but masked in live cells expressing HER2.

Example 5

Figure 7:
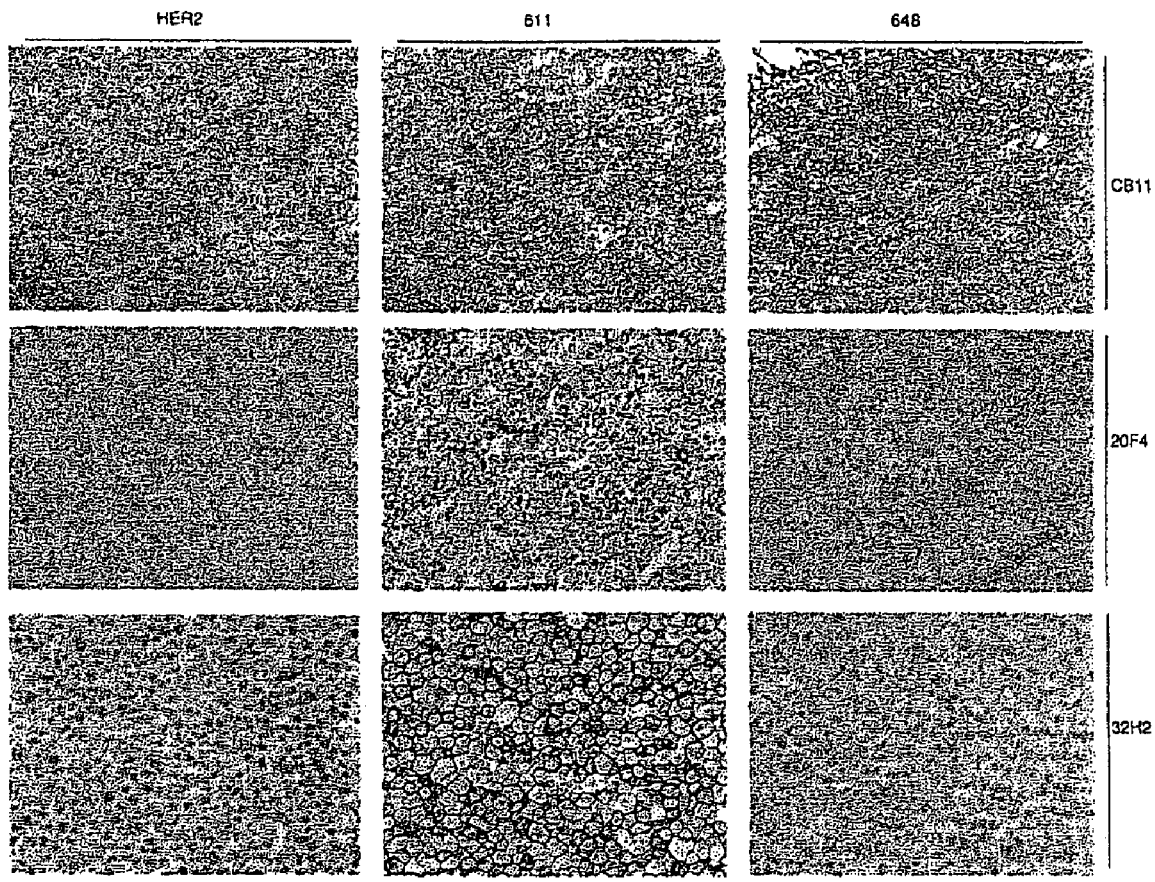
FIG. 7: Characterization of monoclonal antibodies by immunohistochemistry

Characterization of Monoclonal Antibodies Against the N-Terminus of 611-CTF by Immunohistochemistry Immunocytochemical staining of MCF7 cells expressing HER2, 611-CTF or 648-CTF with CB11, an antibody against the cytoplasmic domain of HER2, or with two independent monoclonal anti-611-CTF antibodies raised against the peptide MPIWKFPDEEGASQPSPINSTHSSVDLDDKGC (SEQ ID NO: 4; see FIG. 1) was carried out. The result is shown in FIG. 7.

Conclusions. The epitopes recognized by the antibodies 20F4 and 32H2 is exposed in cells expressing 611-CTF analyzed by immunohistochemistry. In contrast, as judged by the same technique, these epitopes are masked in the full-length HER2 molecule. This result is particularly relevant giving the fact that immunohistochemistry is the technique of choice for most routine test in the clinic.

Example 6

Figure 8:
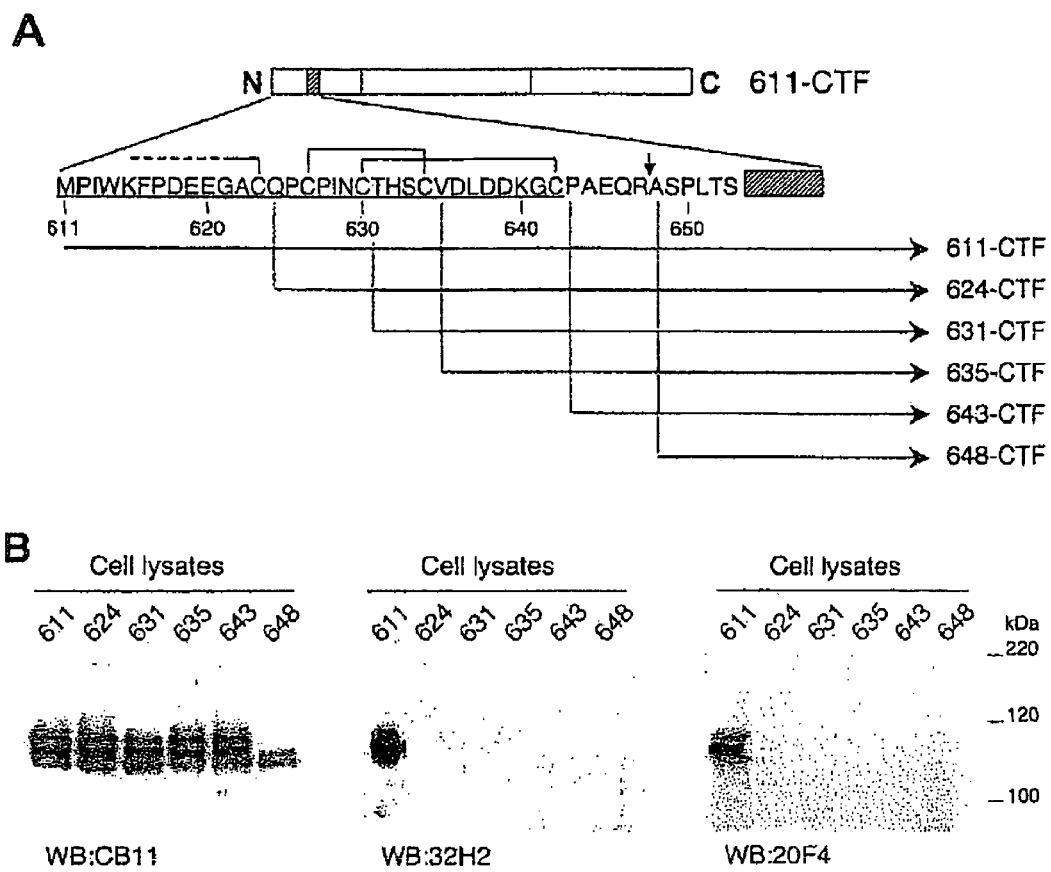
FIG. 8: Characterization of epitopes.

Characterization of the Epitopes Recognized by the Monoclonal Antibodies Against the N-Terminus of 611-CTF (A) Schematic showing the primary sequence of the juxtamembrane region of 611-CTF. The N- and the C-termini of the molecule are indicated. The transmembrane and the kinase domains are indicated by a dashed and a grey box, respectively. The sequence of different deletion constructs is indicated. See FIG. 8(A).

(B) MCF-7 cells transiently transfected with cDNA deletion constructs starting at the indicated amino acids were lysed. Cell lysates were analyzed by Western blot with CB11, an antibody against the cytoplasmic domain of HER2, or with two independent monoclonal anti-611-CTF antibodies raised against the peptide MPIWKFPDEEGASQPSPINSTHSS-VDLDDKGC, (SEQ ID NO: 4) see FIG. 8(B)

Conclusions. The epitopes recognized by the antibodies 32H2 and 20F4 are contained or at least overlap with the sequence MPIWKFPDEEG (SEQ ID NO: 8).

Example 7

Analysis of Human Breast Cancer Samples with a Monoclonal Antibody Against the N-Terminus of 611-CTF or with Herceptest™

Figure 9:
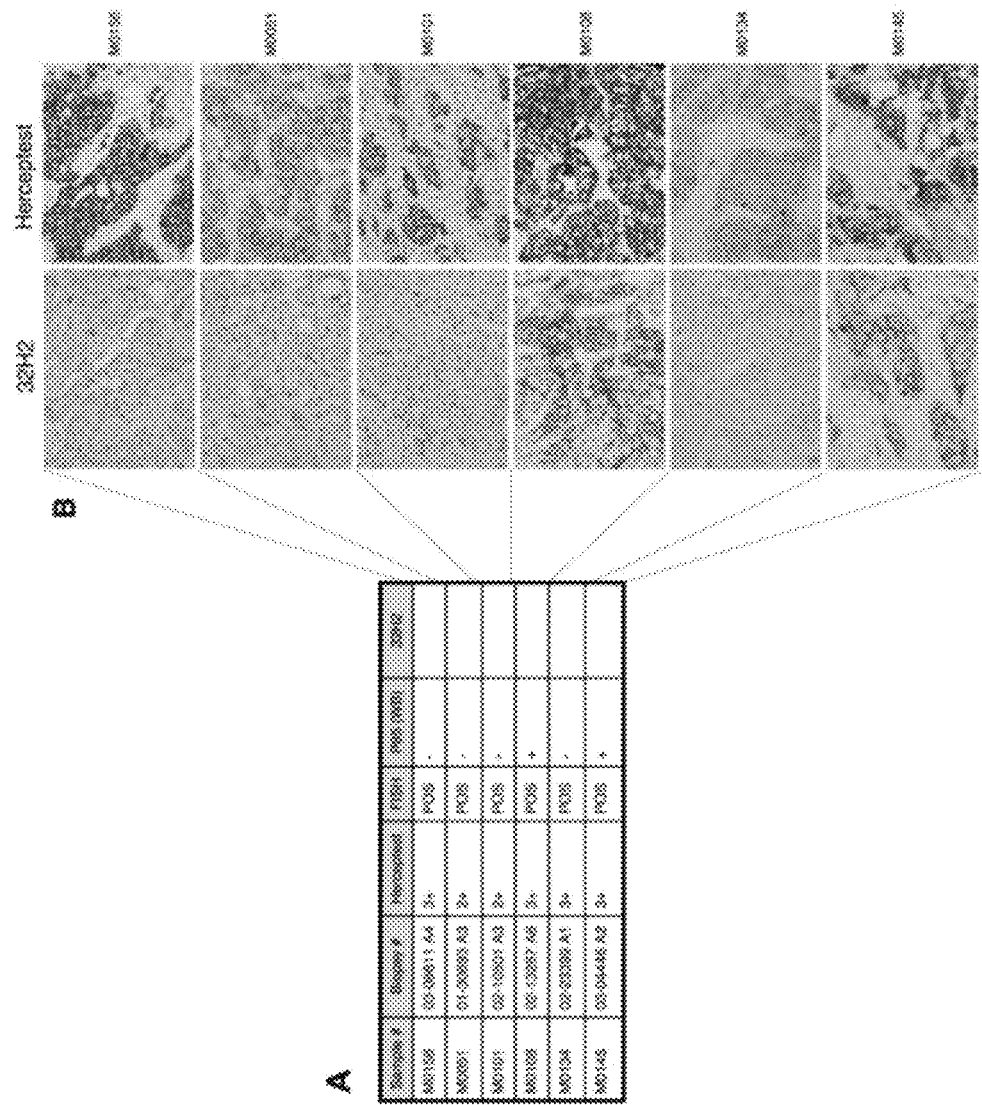
FIG. 9: Analysis of breast cancer samples.

(A) The expression of HER2 in the indicated samples was analyzed with Herceptest™, Fluorescence In Situ Hybridization (FISH) or Western blot. Those samples expressing detectable levels of HER2 carboxy terminal fragments (also known as P95) as judged by Western blot are indicated (see (Scaltriti, M., Rojo, F., Ocana, A., Anido, J., Guzman, M., Cortes, J., Di Cosimo, S., Matias-Guiu, X., Ramon y Cajal, S., Arribas, J., and Baselga, J. (2007) *J Natl Cancer Inst* 99(8), 628-638)). See FIG. 9(A).

(B) Immunocytochemical staining of the same breast cancer samples as in A, with 32H2, a monoclonal anti-611-CTF antibody raised against the peptide MPIWKFPDEE-GASQPSPINSTHSSVDLDDKGC (SEQ ID NO: 4; see FIG. 1) or with HERCEPTEST™, which stains the cytoplasmic domain of HER2. See FIG. 9(B).

Conclusion. By immunohistochemistry; the antibody 32H2 stains human breast cancer samples previously known to express detectable levels of CTFs, as judged by Western blot.

Example 8

Generation of Animal Models to Characterize the Effect of CTF Expression In Vivo Mouse models have been instrumental in showing the oncogenic potential and relevance of HER2 in tumor progression. To characterize its oncogenic potential, we established transgenic (TG) mice expressing 611-CTF under the control of the mouse mammary tumor virus-long terminal repeat, which is preferentially active in the mammary gland. Although the cellular models indicated that soluble intracellular CTFs are inactive, to further explore the consequences of expression of these fragments, we also generated. TG animals expressing 687-CTF. As a control, we used the classical and well-characterized model expressing wild type HER2 (i.e. rat neu).

At age 7 weeks, the levels of 611-CTF expressed in the heterozygous TG 611 lines F3 and F2 were ~ equal to and $\frac{1}{3}^{rd}$, respectively, the levels of endogenous HER2, while the level in F1 was below the detection threshold. The levels of 687-CTF in the homozygous lines developed varied from ~ double to half the levels of HER2 in the TG 687 lines F2 and F1, respectively.

Mammary glands of the TG animals exhibited no macroscopic abnormalities at 7 weeks age. However, morphological examination of carmine-stained whole mounts revealed hyperplasic abnormalities in the mammary ductal trees of TG HER2 mice. Similar abnormalities, albeit less pronounced, were present in all three lines of TG 611 mice. In contrast, the glands of TG 687 mice were indistinguishable from those of wild type mice.

Example 9

611-CTF Expression Leads to the Development of Aggressive Mammary Tumors

Despite the more pronounced hyperplasia in TG HER2 mice, the three lines of TG 611 animals developed more aggressive tumors in terms of number of tumors per animal, tumor growth and tumor onset:

| Mammary Glands | | |
|---|---|---|
| Mice | Average (weeks) | n |
| HER2 (Neu) | 30.3 + 7.5 | 22 |
| 611-F1 | 26.3 ± 4.6 | 6 |
| 611-F2 | 22.2 ± 4.8 | 12 |
| 611-F3 | 23.7 + 5.5 | 3 |

(The appearance of mammary tumors was monitored by palpation weekly.)

No tumors or abnormalities were observed in TG 687 animals even after a follow-up of more than one year.

Histological analysis of the tumors showed the same typical invasive solid nodular carcinomas induced by HER2 in the TG 611 mice. The only histological difference between the tumors initiated by HER2 and 611-CTF was a higher number of mitotic images in the ones from TG 611 mice.

As previously shown, TG HER2 mice developed lung metastasis. Three to six weeks after detection of tumors, $\sim \frac{1}{4}^{th}$ of the TG HER2 animals had detectable nodules in the lungs:

| Mice | Lung metastasis | n |
|---|---|---|
| HER2 (Neu) | 22 | 9 |
| 611-F1, F2, F3 | 56 | 9 |

(Mice were sacrificed 3-6 weeks after tumor detection by palpation, and the appearance of metastasis monitored by immnunohistochemistry).

Histological analysis of the lung metastases confirmed the expression of HER2 and staining with cytokeratin 18 verified that the cells originated from the primary tumor. In comparison to TG HER2, the number of animals expressing 611-CTF with detectable metastases was more than double. This shows that the tumors initiated by this CTF have a more pronounced tendency to invade the lungs.

Sequences

```
Met Pro Ile Trp Lys Phe Pro Asp Glu Glu Gly Ala Cys Gln Pro Cys    SEQ ID NO: 1
1               5                  10                  15

Pro Ile Asn Cys Thr His Ser Cys Val Asp Leu Asp Asp Lys Gly Cys
                20                  25                  30

Pro Ala Glu Gln Arg Ala Ser Pro Leu Thr Ser Ile Val Ser Ala Val
                35                  40                  45

Val Gly Ile Leu Leu Val Val Leu Gly Val Val Phe Gly Ile Leu
        50                  55                  60

Ile Lys Arg Arg Gln Gln Lys Ile Arg Lys Tyr Thr Met Arg Arg Leu
65                  70                  75                  80

Leu Gln Glu Thr Glu Leu Val Glu Pro Leu Thr Pro Ser Gly Ala Met
                85                  90                  95
```

-continued

```
Pro Asn Gln Ala Gln Met Arg Ile Leu Lys Glu Thr Glu Leu Arg Lys
            100                 105                 110

Val Lys Val Leu Gly Ser Gly Ala Phe Gly Thr Val Tyr Lys Gly Ile
        115                 120                 125

Trp Ile Pro Asp Gly Glu Asn Val Lys Ile Pro Val Ala Ile Lys Val
    130                 135                 140

Leu Arg Glu Asn Thr Ser Pro Lys Ala Asn Lys Glu Ile Leu Asp Glu
145                 150                 155                 160

Ala Tyr Val Met Ala Gly Val Gly Ser Pro Tyr Val Ser Arg Leu Leu
                165                 170                 175

Gly Ile Cys Leu Thr Ser Thr Val Gln Leu Val Thr Gln Leu Met Pro
            180                 185                 190

Tyr Gly Cys Leu Leu Asp His Val Arg Glu Asn Arg Gly Arg Leu Gly
        195                 200                 205

Ser Gln Asp Leu Leu Asn Trp Cys Met Gln Ile Ala Lys Gly Met Ser
    210                 215                 220

Tyr Leu Glu Asp Val Arg Leu Val His Arg Asp Leu Ala Ala Arg Asn
225                 230                 235                 240

Val Leu Val Lys Ser Pro Asn His Val Lys Ile Thr Asp Phe Gly Leu
                245                 250                 255

Ala Arg Leu Leu Asp Ile Asp Glu Thr Glu Tyr His Ala Asp Gly Gly
            260                 265                 270

Lys Val Pro Ile Lys Trp Met Ala Leu Glu Ser Ile Leu Arg Arg Arg
        275                 280                 285

Phe Thr His Gln Ser Asp Val Trp Ser Tyr Gly Val Thr Val Trp Glu
    290                 295                 300

Leu Met Thr Phe Gly Ala Lys Pro Tyr Asp Gly Ile Pro Ala Arg Glu
305                 310                 315                 320

Ile Pro Asp Leu Leu Glu Lys Gly Glu Arg Leu Pro Gln Pro Pro Ile
                325                 330                 335

Cys Thr Ile Asp Val Tyr Met Ile Met Val Lys Cys Trp Met Ile Asp
            340                 345                 350

Ser Glu Cys Arg Pro Arg Phe Arg Glu Leu Val Ser Glu Phe Ser Arg
        355                 360                 365

Met Ala Arg Asp Pro Gln Arg Phe Val Val Ile Gln Asn Glu Asp Leu
    370                 375                 380

Gly Pro Ala Ser Pro Leu Asp Ser Thr Phe Tyr Arg Ser Leu Leu Glu
385                 390                 395                 400

Asp Asp Asp Met Gly Asp Leu Val Asp Ala Glu Glu Tyr Leu Val Pro
                405                 410                 415

Gln Gln Gly Phe Phe Cys Pro Asp Pro Ala Pro Gly Ala Gly Gly Met
            420                 425                 430

Val His His Arg His Arg Ser Ser Ser Thr Arg Ser Gly Gly Gly Asp
        435                 440                 445

Leu Thr Leu Gly Leu Glu Pro Ser Glu Glu Ala Pro Arg Ser Pro
    450                 455                 460

Leu Ala Pro Ser Glu Gly Ala Gly Ser Asp Val Phe Asp Gly Asp Leu
465                 470                 475                 480

Gly Met Gly Ala Ala Lys Gly Leu Gln Ser Leu Pro Thr His Asp Pro
                485                 490                 495

Ser Pro Leu Gln Arg Tyr Ser Glu Asp Pro Thr Val Pro Leu Pro Ser
            500                 505                 510

Glu Thr Asp Gly Tyr Val Ala Pro Leu Thr Cys Ser Pro Gln Pro Glu
        515                 520                 525
```

```
Tyr Val Asn Gln Pro Asp Val Arg Pro Gln Pro Ser Pro Arg Glu
    530                 535                 540

Gly Pro Leu Pro Ala Ala Arg Pro Ala Gly Ala Thr Leu Glu Arg Ala
545                 550                 555                 560

Lys Thr Leu Ser Pro Gly Lys Asn Gly Val Val Lys Asp Val Phe Ala
                565                 570                 575

Phe Gly Gly Ala Val Glu Asn Pro Glu Tyr Leu Thr Pro GLn Gly Gly
                580                 585                 890

Ala Ala Pro Gln Pro His Pro Pro Ala Phe Ser Pro Ala Phe Asp
                595                 600                 605

Asn Leu Tyr Tyr Trp Asp Gln Asp Pro Pro Glu Arg Gly Ala Pro Pro
    610                 615                 620

Ser Thr Phe Lys Gly Thr Pro Thr Ala Glu Asn Pro Glu Tyr Leu Gly
625                 630                 635                 640

Leu Asp Val Pro Val
                645

Met Pro Ile Trp Lys Phe Pro Asp Glu Glu Gly Ala Cys Gln Pro Cys    SEQ ID NO: 2
1               5                   10                  15

Pro Ile Asn Cys Thr His Ser Cys Val Asp Leu Asp Asp Lys Gly Cys
                20                  25                  30

Pro Ala Glu Gln Arg Ala Ser Pro Leu Thr
            35                  40

Met Pro Ile Trp Lys Phe Pro Asp Glu Glu Gly Ala Cys Gln Pro Cys    SEQ ID NO: 3
1               5                   10                  15

Pro Ile Asn Cys Thr His Ser Cys Val Asp Leu Asp Asp Lys Gly Cys
                20                  25                  30

Met Pro Ile Trp Lys Phe Pro Asp Glu Glu Gly Ala Ser Gln Pro Ser    SEQ ID NO: 4
1               5                   10                  15

Pro Ile Asn Ser Thr His Ser Ser Val Asp Leu Asp Asp Lys Gly Cys
                20                  25                  30

Met Pro Ile Trp Lys Phe Pro Asp Glu Glu Gly Ala Ser                SEQ ID NO: 5
1               5                   10
```

SEQUENCE LISTING FREE TEXT

SEQ ID NO: 1 Truncated form or Carboxy Terminal Fragment (CTF) of the human protein HER 2

SEQ ID NO: 2 Epitope of a truncated form of the human HER2 protein

SEQ ID NO: 3 Epitope of a truncated form of the human HER2 protein

SEQ ID NO: 4. Synthetic peptide derived from an epitope of a truncated form of the human HER2 protein SEQ ID NO: 5 Synthetic peptide derived from an epitope of a truncated form of the human HER2 protein

The invention claimed is:

1. An isolated monoclonal antibody or fragment thereof that recognizes an epitope of a truncated form of HER2 receptor, produced by the hybridoma cell line deposited with the "Deutschland Sammlung von Mikroorganismen und Zellen—DSMZ" with access number DSM ACC2904 or the hybridoma cell line deposited with the "Deutschland Sammlung von Mikroorganismen und Zellen—DSMZ" with access number DSM ACC2980.

2. The antibody or fragment according to claim 1, wherein the fragment is one selected from the group consisting of F(ab), F(ab') and Fv.

3. An agent for diagnosis and determination of prognosis in isolated samples of cancers of the type that express the HER2 receptor or its truncated variants, which comprises at least one antibody or a fragment thereof according claim 1.

4. The agent for diagnosis according to claim 3, wherein the antibody or fragment thereof is arranged on a solid support.

5. A kit for diagnosis and determination of prognosis in isolated samples of cancers of the type that express the HER2 receptor or its truncated variants, wherein said kit comprises at least one antibody or a fragment thereof according to claim 1 for detecting the presence in the sample of a truncated form of HER2 receptor.

6. The kit for diagnosis and determination of prognosis according to claim 5, wherein the antibody or fragment thereof is arranged on a solid support.

7. The kit for diagnosis and determination of prognosis according to claim 5, wherein said kit comprises components for determining differential migration of the truncated form of HER2 receptor of SEQ ID NO: 1, in relation to the complete form of said HER2 receptor.

8. The kit for diagnosis and determination of prognosis according to claim 5, further comprising reagents, buffers, detection solutions and detailed instructions for use thereof.

9. A pharmaceutical composition comprising an antibody or a fragment thereof according to claim 8 and at least one pharmaceutically acceptable excipient and/or vehicle.

10. An isolated monoclonal antibody or fragment thereof that recognizes an epitope of a truncated form of HER2 receptor, selected from the monoclonal antibodies consisting of 20F4 deposited with hybridoma access number DSM ACC2904 and 32H2 deposited with hybridoma access number DSM ACC2980.

11. An agent for diagnosis and determination of prognosis of cancer in isolated samples of cancers of the type that express HER2 receptor or its truncated variants, comprising at least one antibody or a fragment thereof according to claim 10.

12. A kit for diagnosis and determination of prognosis of cancer in isolated samples of cancers of the type that express the HER2 receptor or its truncated variants, comprising an antibody or fragment thereof according to claim 10.

13. The kit of claim 12, further comprising reagents, buffers, detection solutions and detailed instructions for use thereof.

14. A hybridoma producing the monoclonal antibody of claim 1.

15. A method for producing an isolated monoclonal antibody or fragment thereof that recognizes an epitope of a truncated form of HER2 receptor comprising
   immunizing a mammal with a peptide that consists of SEQ ID NO: 3 or SEQ ID NO:4, which peptide is conjugated with an immunogen;
   producing a hybridoma cell line;
   growing the hybridoma cell line in a suitable culture medium; and
   recovering the monoclonal antibody from the culture medium.

16. A method for obtaining a monoclonal antibody, comprising growing the hybridoma cell line according to claim 14 in a suitable culture medium and recovering the monoclonal antibody from said culture medium.

17. A method of cancer diagnosis, which comprises the detection of the presence of the HER2 receptor truncated form consisting of the amino acid sequence SEQ ID NO: 1 in a patient sample, wherein said detection comprises contacting said patient sample with an antibody of claim 1 and detecting the binding of said antibody to said sample.

18. The method according to claim 17, which is a prognostic method allowing the prognosis of progression of tumor growth and/or metastases.

* * * * *